US008929998B2

(12) United States Patent
Burgher et al.

(10) Patent No.: US 8,929,998 B2
(45) Date of Patent: Jan. 6, 2015

(54) PERCUTANEOUS PLACEMENT OF ELECTRODES

(75) Inventors: Abram H. Burgher, Scottsdale, AZ (US); Marc A. Huntoon, Franklin, TN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 320 days.

(21) Appl. No.: 13/498,873

(22) PCT Filed: Sep. 23, 2010

(86) PCT No.: PCT/US2010/050055
§ 371 (c)(1),
(2), (4) Date: Apr. 17, 2012

(87) PCT Pub. No.: WO2011/041203
PCT Pub. Date: Apr. 7, 2011

(65) Prior Publication Data
US 2012/0197372 A1    Aug. 2, 2012

Related U.S. Application Data

(60) Provisional application No. 61/277,866, filed on Sep. 30, 2009.

(51) Int. Cl.
*A61N 1/00* (2006.01)
*A61N 1/05* (2006.01)
*A61B 19/00* (2006.01)
*A61N 1/36* (2006.01)

(52) U.S. Cl.
CPC ....... *A61N 1/0558* (2013.01); *A61B 2019/5276* (2013.01); *A61N 1/36017* (2013.01); *A61N 1/36021* (2013.01)
USPC ........................... 607/118; 607/117; 607/116

(58) Field of Classification Search
CPC .. A61N 1/0556; A61N 1/0551; A61N 1/0558
USPC ......................................... 607/118, 117, 116
See application file for complete search history.

(56) References Cited

U.S. PATENT DOCUMENTS 5,265,608 A    11/1993    Lee et al.
5,462,545 A    10/1995    Wang et al.
(Continued)

FOREIGN PATENT DOCUMENTS

JP      4469926 B2      3/2010
WO      WO9729802 A2    8/1997

OTHER PUBLICATIONS

International Preliminary Report on Patentability ; Apr. 3, 2012; World Intellectual Property Organization (WIPO) (International Bureau of); PCT/US2010/050055; 5 pages.

(Continued)

*Primary Examiner* — Christopher D Koharski
*Assistant Examiner* — Philip Edwards
(74) *Attorney, Agent, or Firm* — Fish & Richardson P.C.

(57) ABSTRACT

This document relates to methods and materials involved in delivering therapies to target tissue (e.g., a peripheral nerve). For example, methods and materials for placing and subsequently using leads to deliver electrical and/or drug therapies to target tissues (e.g., nerves and/or arteries) are provided.

18 Claims, 35 Drawing Sheets

(56) References Cited

U.S. PATENT DOCUMENTS

| | | | |
|---|---|---|---|
| 6,061,596 A | 5/2000 | Richmond et al. | |
| 6,181,965 B1 | 1/2001 | Loeb et al. | |
| 6,505,075 B1 | 1/2003 | Weiner | |
| 6,577,904 B1 * | 6/2003 | Zhang et al. | 607/116 |
| 7,349,743 B2 | 3/2008 | Tadlock | |
| 2003/0088301 A1 | 5/2003 | King | |
| 2004/0243206 A1 | 12/2004 | Tadlock | |
| 2005/0033393 A1 | 2/2005 | Daglow | |
| 2005/0085870 A1 | 4/2005 | Goroszeniuk | |
| 2005/0096718 A1 | 5/2005 | Gerber et al. | |
| 2006/0167416 A1 | 7/2006 | Mathis et al. | |
| 2007/0073356 A1 | 3/2007 | Rooney et al. | |
| 2007/0173900 A1 | 7/2007 | Siegel et al. | |
| 2007/0219608 A1 | 9/2007 | Swoyer et al. | |
| 2008/0065182 A1 | 3/2008 | Strother et al. | |
| 2008/0103576 A1 | 5/2008 | Gerber | |
| 2008/0132982 A1 * | 6/2008 | Gerber | 607/118 |
| 2008/0188916 A1 | 8/2008 | Jones et al. | |
| 2008/0195092 A1 | 8/2008 | Kim et al. | |
| 2008/0269716 A1 | 10/2008 | Bonde et al. | |
| 2009/0132017 A1 | 5/2009 | Erickson et al. | |
| 2009/0222053 A1 | 9/2009 | Gaunt et al. | |

OTHER PUBLICATIONS

International Search Report and Written Opinion; Jun. 3, 2011; World Intellectual Property Organization (WIPO) (International Bureau of); PCT/US2010/050055; 10 pages.

Huntoon; Feasibility of ultrasound-guided percutaneous placement of peripheral nerve stimulation electrodes and anchoring during simulated movement: part two, upper extremity; Reg Anesth Pain Med; Nov.-Dec. 2008; 33(6):558-565.

* cited by examiner

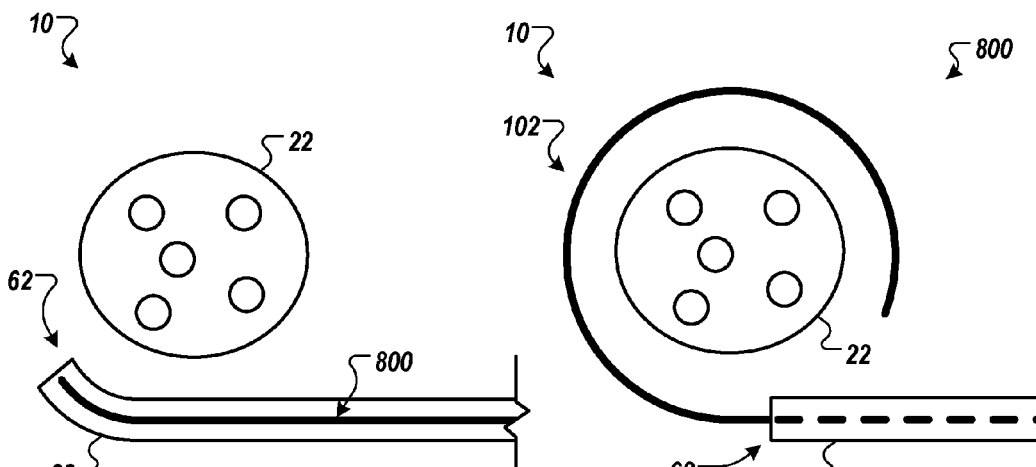
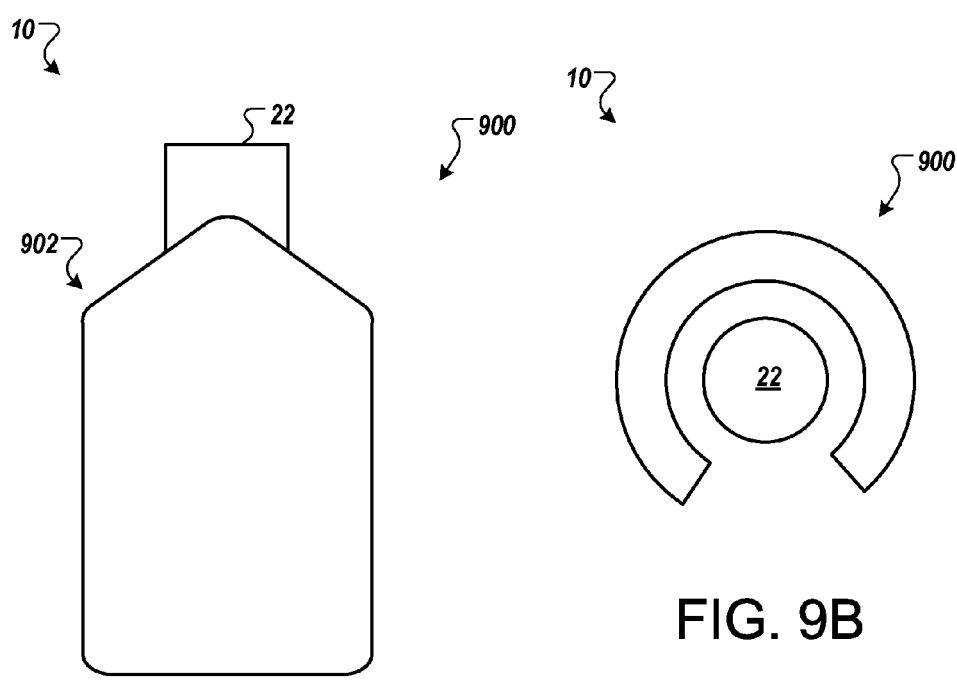
FIG. 8A  FIG. 8B
FIG. 9A  FIG. 9B

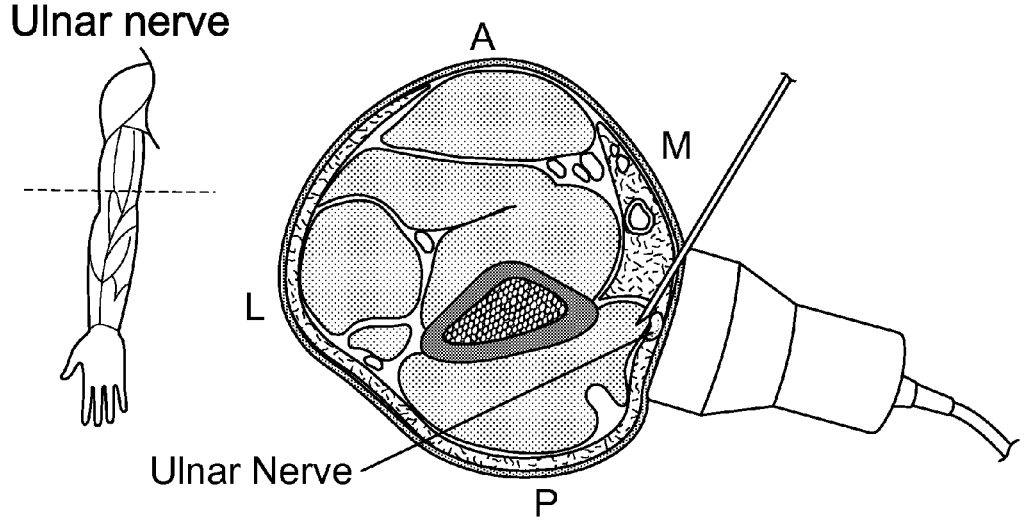
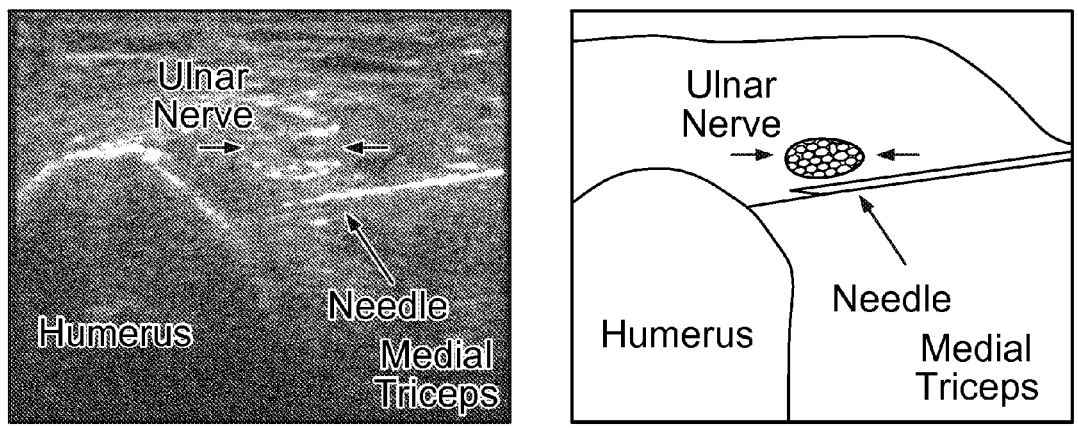
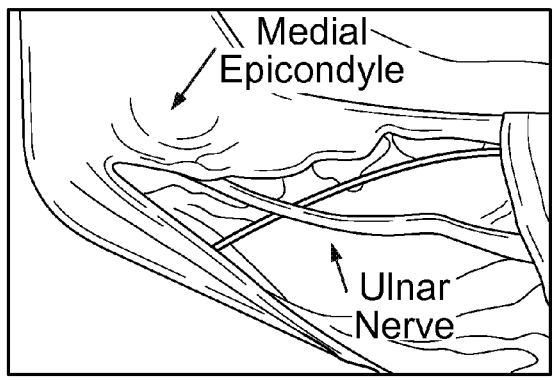
FIG. 19

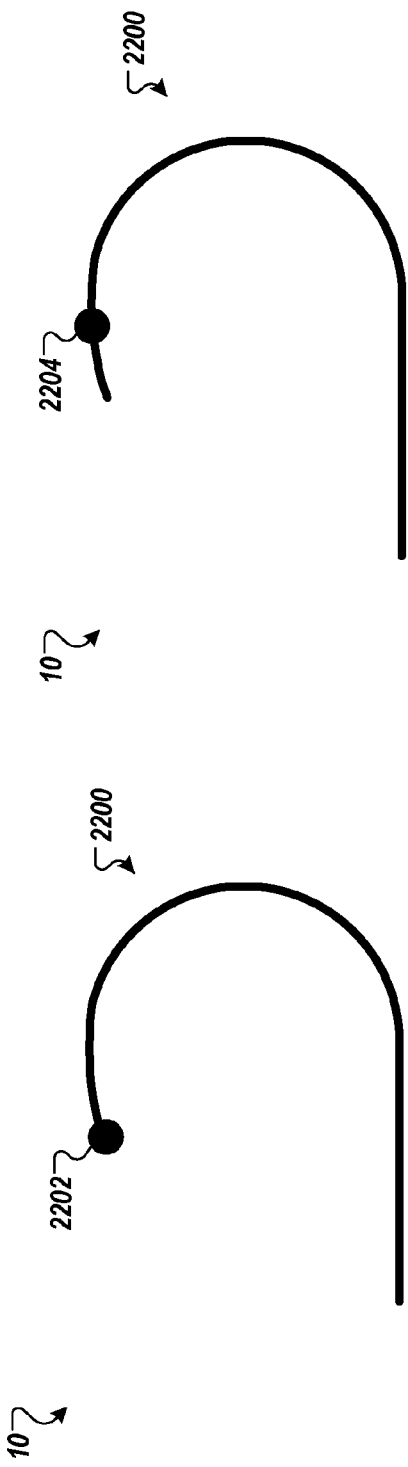
FIG. 22A
FIG. 22B
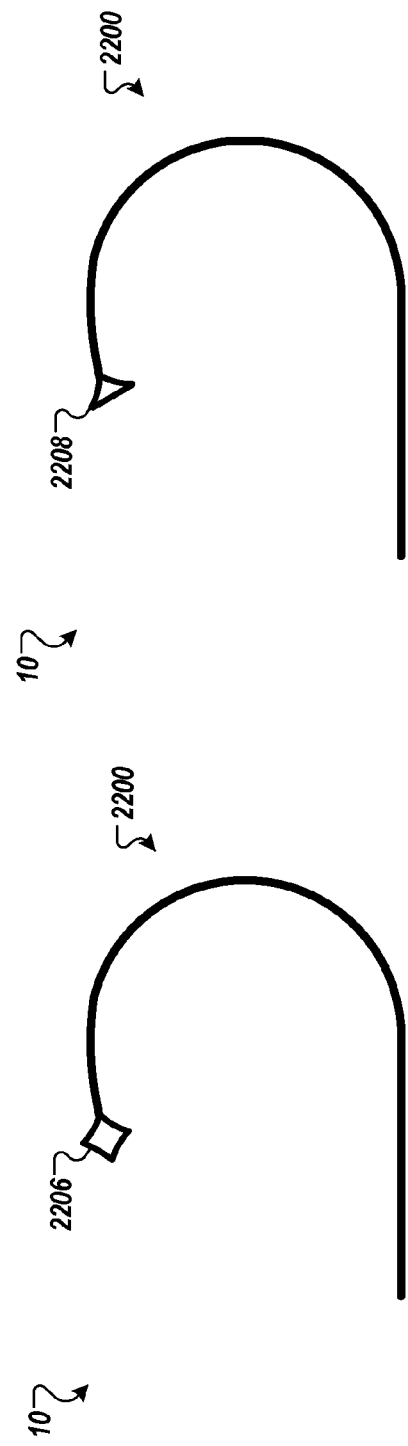
FIG. 22C
FIG. 22D

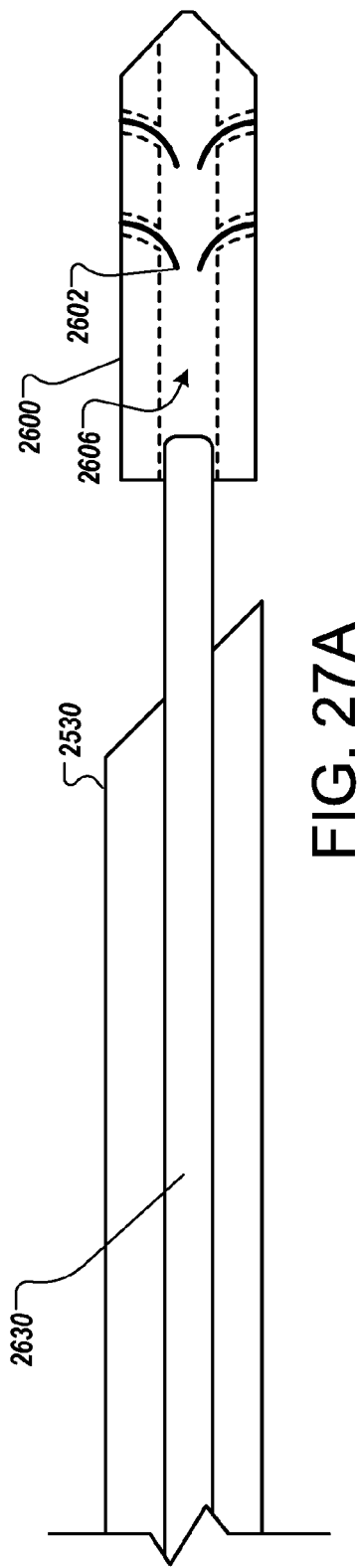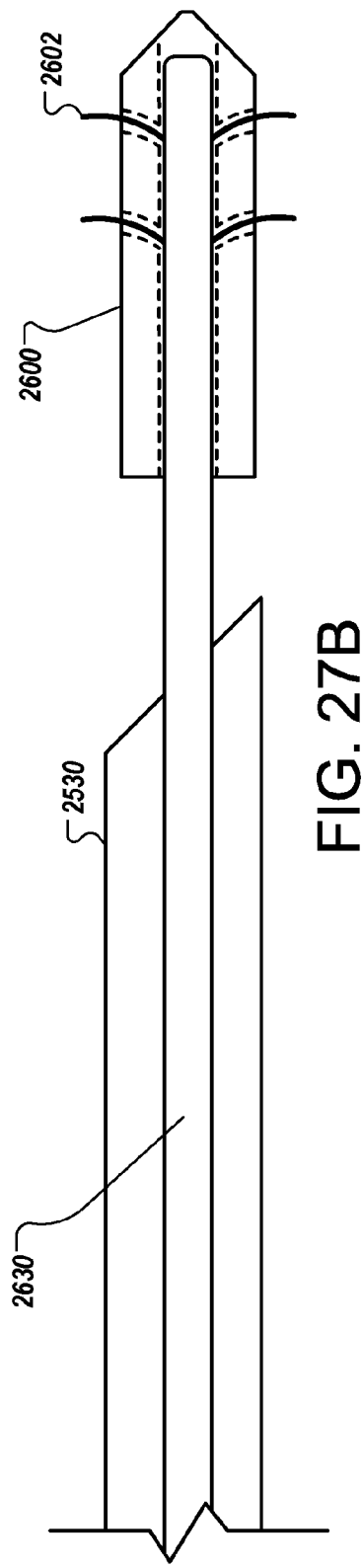

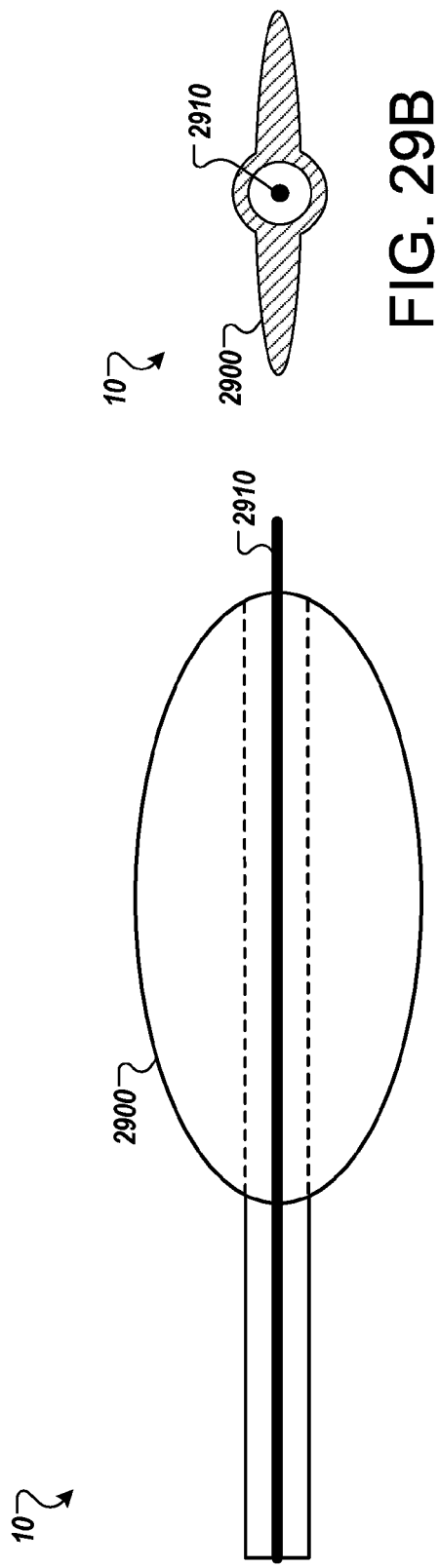
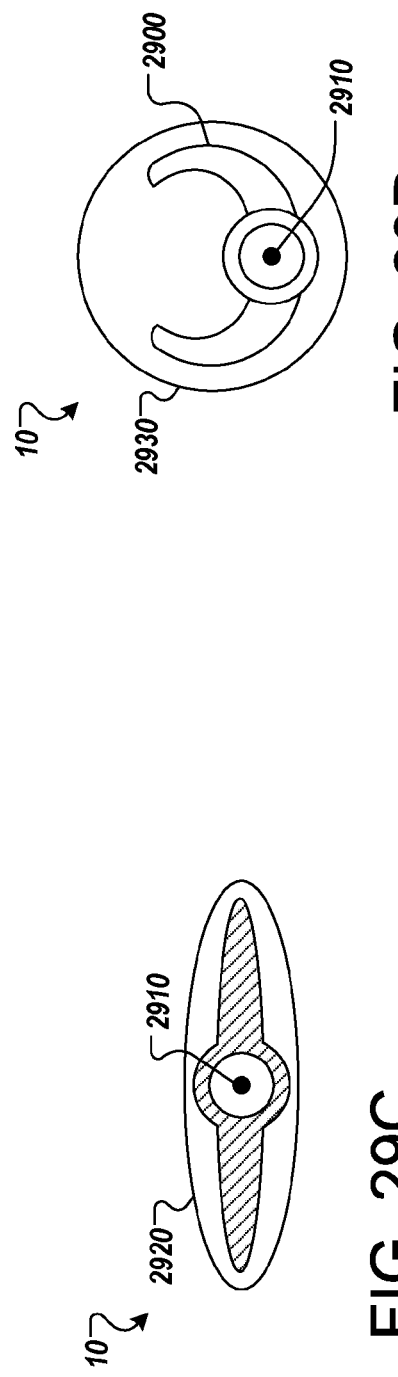
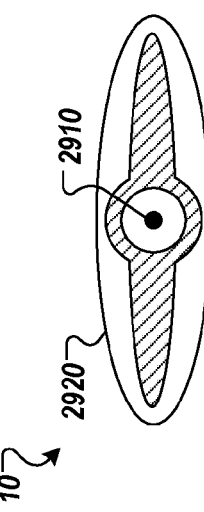
FIG. 29A  FIG. 29B  FIG. 29C  FIG. 29D

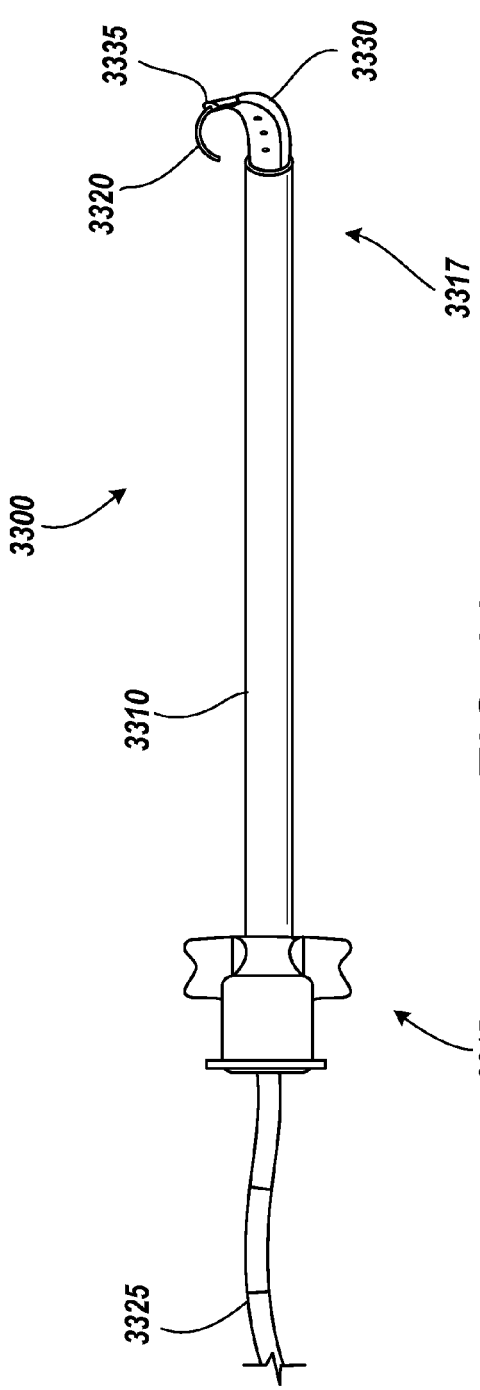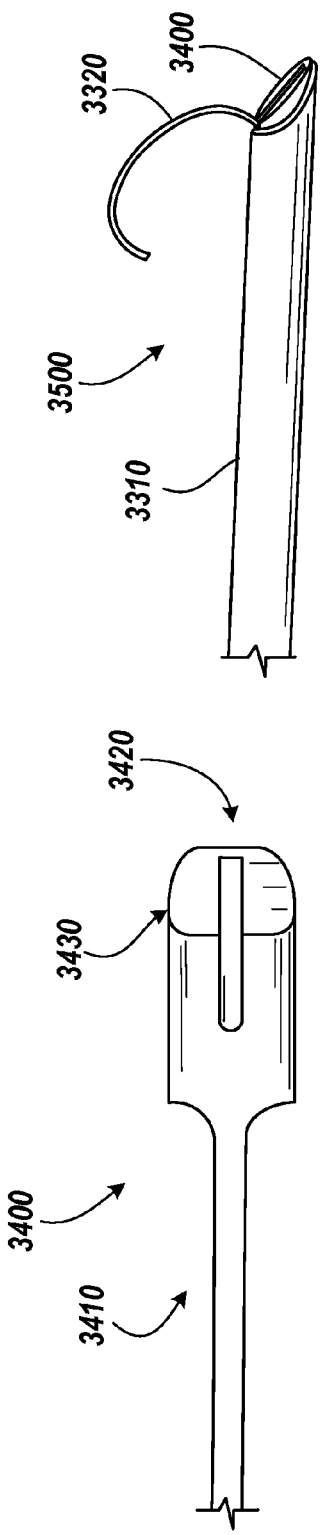
FIG. 33
FIG. 35
FIG. 34

PERCUTANEOUS PLACEMENT OF ELECTRODES

CROSS REFERENCE TO RELATED APPLICATIONS

This application is a National Stage application under 35 U.S.C. 371 and claims benefit under 35 U.S.C. 119(a) of International Application No. PCT/US2010/050055, having an International Filing Date of Sep. 23, 2010, which claims the benefit of priority to U.S. Provisional Application Ser. No. 61/277,866, filed Sep. 30, 2009. The disclosures of the prior applications are considered part of (and are incorporated by reference in) the disclosure of this application.

BACKGROUND

1. Technical Field

This document relates to methods and materials involved in delivering therapies to nerve tissue (e.g., peripheral nerve tissue) and/or vascular tissue or perivascular nervous tissues (e.g., neurovascular tissue of the carotid bifurcation (carotid sinus), femoral arteries, popliteal arteries, or renal arteries). For example, this document relates to methods and materials for placing and using leads to deliver electrical and/or drug therapies to nerves (e.g., peripheral nerves) or vascular tissue.

2. Background Information

Peripheral nerve entrapment syndromes, surgical iatrogenic injuries, trauma, and injection injuries can cause peripheral nerve pain requiring treatment. Peripheral nerve stimulation (PNS) is a neuromodulation technique that includes applying an electrical current to the peripheral nerves to ameliorate chronic pain.

SUMMARY

This document relates to methods and materials involved in delivering therapies to nerve tissue (e.g., peripheral nerve tissue) and/or vascular tissue or perivascular nervous tissues (e.g., neurovascular tissue of the carotid bifurcation (carotid sinus), femoral arteries, popliteal arteries, or renal arteries). For example, this document provides methods and materials for placing and using leads to deliver electrical and/or drug therapies to nerves (e.g., peripheral nerves) or vascular tissue.

In general, one aspect of this document features a method for providing peripheral nerve stimulation. The method comprises, or consists essentially of, (a) percutaneously wrapping a lead comprising an electrode at least 180 degrees around a peripheral nerve within a mammal, and (b) applying electrical stimulation to the peripheral nerve via the electrode. The lead can be a curved lead when positioned at least 180 degrees around the peripheral nerve within the mammal. The curved lead can comprise more than one arc dimension when positioned at least 180 degrees around the peripheral nerve within the mammal. In some cases, the lead can be positioned to not be in contact with the peripheral nerve when positioned at least 180 degrees around the peripheral nerve within the mammal. In some cases, the lead can be in contact with the peripheral nerve when positioned at least 180 degrees around the peripheral nerve within the mammal. The lead can be insulated or not insulated. The lead can comprise two or more electrodes. The lead can comprise an array of electrodes. The method can comprise percutaneously wrapping the lead at least 270 degrees around the peripheral nerve within the mammal. The method can comprise percutaneously wrapping the lead at least 360 degrees around the peripheral nerve within the mammal. The method can comprise percutaneously wrapping the lead at least 360 degrees around the peripheral nerve in a corkscrew configuration. The method can comprise percutaneously wrapping the lead around the peripheral nerve in a manner such that the lead surrounds the peripheral nerve in at least one cross-sectional plane of the peripheral nerve. The lead can comprise an anchor. The anchor can be self-deployable. The anchor can comprise a corkscrew shape or a barb shape. The lead can comprise more than one anchor. The lead can comprise an echogenic material or an echogenic marking. The lead can be implanted into position within the mammal using ultrasound-guided placement. The lead can comprise the ability to release a drug into the mammal. The drug can be selected from the group consisting of GABA agonists, alpha-2 agonists, neuropeptide antagonists, angiogenesis inhibitors, nerve growth factor inhibitors, anti-inflammatory agents (e.g., cytokine/chemokine antagonists), genetic materials, and anesthetics. The lead can contain the drug, and the drug can be eluted from the lead over time. The lead can comprise a lumen and define at least one exit port in fluid communication with the lumen, wherein the exit port is located near the peripheral nerve when the lead is positioned at least 180 degrees around the peripheral nerve within the mammal. The lead can be attached to a reservoir containing the drug, and the lumen is in fluid communication with the reservoir. A valve can be positioned in the lumen or the reservoir to control the release of the drug from the reservoir to the exit port. The lead can be flexible and paddle shaped. The lead can comprise a shape-memory material. The shape-memory material can be nitinol. The lead can be steerable. In some cases, no more than one skin port can be used to percutaneously wrap the lead at least 180 degrees around the peripheral nerve within the mammal. Two skin ports can be used to percutaneously wrap the lead at least 180 degrees around the peripheral nerve within the mammal. A trocar, sheath, or stylet can be used to advance the lead into the mammal. The lead can define a lumen. The method can comprise advancing a tubular member defining a lumen to the peripheral nerve, advancing a wire through the lumen of the tubular member and at least 180 degrees around the peripheral nerve, and advancing the lead over the wire. The tubular member can be a needle. The wire can be a shape-memory wire. The shape-memory wire can be a nitinol wire. The method can comprise withdrawing the tubular member before the lead is advanced over the wire. The method can comprise withdrawing the wire after the lead is advanced over the wire.

In another aspect, this document features a system for percutaneously providing peripheral nerve stimulation. The system comprises (a) a shape-memory wire configured to form a shape that wraps at least 180 degrees around a peripheral nerve within a mammal, (b) a tubular member defining a lumen sized to receive the shape-memory wire, and (c) a lead comprising an electrode and defining a lumen sized to be advanced over the shape-memory wire when the shape-memory wire is in a position that wraps at least 180 degrees around the peripheral nerve within the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 8A/B-9A/B depict therapeutic leads including shape memory materials, in accordance with some embodiments.

FIG. 19. Upper panel: a cross section though the lower third of the upper arm shows the approach to ultrasound-guided electrode placement for the ulnar nerve. Middle panel, left: the needle shaft is passing inferior to the ulnar nerve approximately 12 cm above the medial epicondyle. The medial triceps muscle tissue is inferior to the lead and the nerve; right: the line drawing depicts the relationships seen on ultrasound image. Lower panel: the lead contacts are clearly seen under the nerve on gross dissection. The proximal portion of the lead can be seen to have a thin "film" of triceps muscle tissue that has been passed through. A, anterior; L, lateral; M, medial; P, posterior.

FIGS. 22A-D depict various lead wires used in an electrode system, including features to reduce lead travel, in accordance with some embodiments.

FIGS. 27A-B depict electrode systems, including anchors to reduce lead travel, in accordance with some embodiments.

FIGS. 29A-D depict paddle leads used in an electrode system, in accordance with some embodiments.

FIG. 33 is a photograph of an electrode system, in accordance with some embodiments.

FIG. 34 is a photograph of an exemplary insert device configured to hold a wire in proper orientation in a delivery needle.

FIG. 35 is a photograph of an exemplary system having a delivery needle, a wire, and an insert device configured to hold the wire in proper orientation within the delivery needle.

DETAILED DESCRIPTION

This document provides methods and materials involved in delivering therapies to tissues such as nerve tissue and/or vascular tissue. For example, this document provides methods and materials for placing and using leads to deliver electrical and/or drug therapies to nerve tissue and/or vascular tissue. The methods and materials provided herein can be configured to deliver a therapy to any appropriate tissue including, without limitation, nerve tissue and vascular tissue. For example, the methods and materials provided herein can used to deliver a therapy to nerves such as peripheral nerves (e.g., radial, ulnar, median, sciatic, femoral, peroneal, and phrenic nerves) or cranial nerves (e.g. vagus nerve). In some cases, the methods and materials provided herein can used to deliver a therapy to vascular tissue such as femoral arteries, popliteal arteries, and renal arteries or to neural tissue of the carotid bifurcation (e.g. carotid sinus). In some cases, the methods and materials provided herein can used to deliver a therapy to non-nervous, non-vascular tissue such as tendons, ligaments, or bone.

Figure 1A:
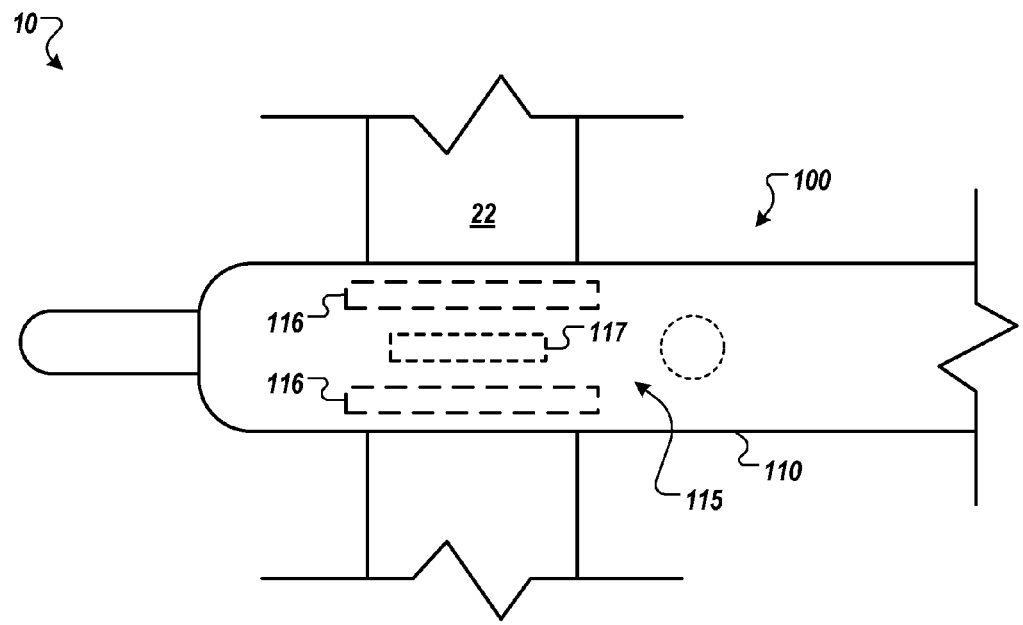
FIGS. 1A-C depict an electrode system for use in single port placement, in accordance with some embodiments.
Figure 1B:
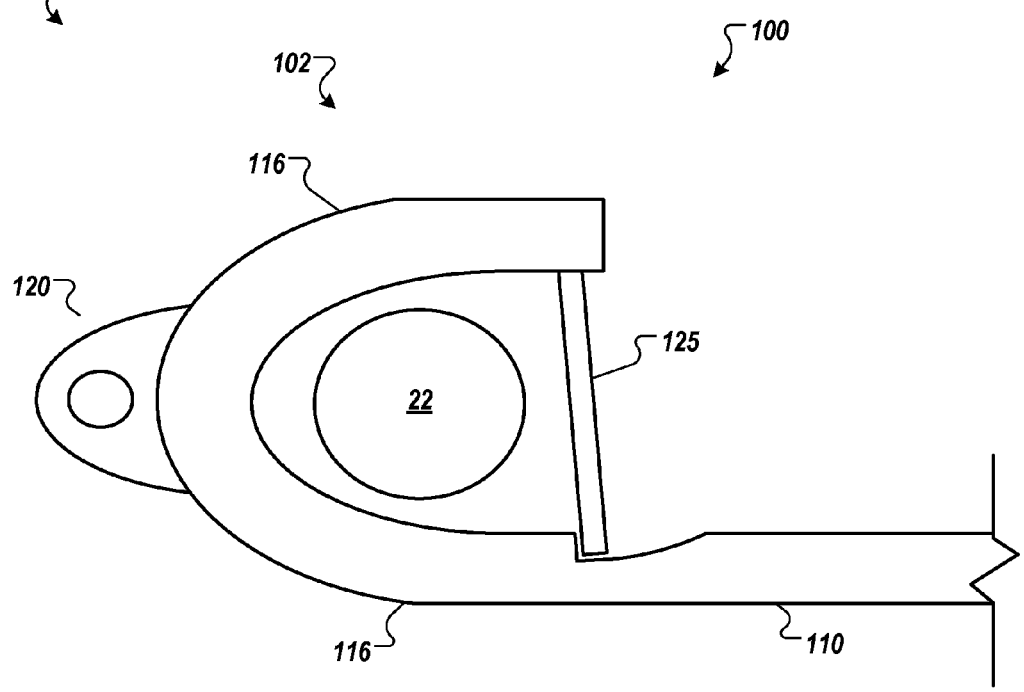

Referring now to FIGS. 1A-B, portions of an electrode system 10 can be delivered percutaneously and used to deliver therapy to a patient. In some embodiments, ultrasound imaging can be used to place electrode system 10. For example, a portion of electrode system 10 can be delivered through the inner lumen of a needle, guided by ultrasound imaging, to a peripheral nerve where electrode system 10 can circumnavigate the nerve. In some cases, an electrode system provided herein can completely surround a portion of a tissue to be treated (e.g., a peripheral nerve, vein, or artery), while in other cases, an electrode system provided herein can partially surround a portion of a tissue to be treated (e.g., a peripheral nerve, vein, or artery). For example, a lead of an electrode system provided herein can be wrapped at least 180 degrees (e.g., at least 200 degrees, at least 220 degrees, at least 240 degrees, at least 250 degrees, at least 260 degrees, at least 270 degrees, at least 280 degrees, at least 290 degrees, at least 300 degrees, at least 310 degrees, at least 320 degrees, at least 330 degrees, at least 340 degrees, at least 350 degrees, or at least 355 degrees) around a tissue to be treated (e.g., a peripheral nerve, vein, or artery) within a mammal. Once surrounding or partially surrounding a portion of a tissue to be treated (e.g., a radial nerve), electrode system 10 can be used to deliver therapeutic electrical stimulation, therapeutic drugs, and the like to the tissue (e.g., nerve). These therapies can be used in the management of pain, the treatment of obesity, cosmetic applications, and the like. Minimally invasive techniques, such as those utilizing electrode system 10 can advantageously reduce trauma associated with open surgical dissection and stimulator placement. In some cases, ultrasonic imaging techniques can be utilized to improve the accuracy of stimulator placement.

In some embodiments, electrode system 10 can include a flexible paddle lead 100 that can be delivered through the interior lumen of a needle to a target tissue (e.g., a peripheral nerve) of a patient (e.g., a human patient). Lead 100 can include an elongate lead body 110, which can contain one or more electrodes 115 (e.g., including one or more anodes 116 and one or more cathodes 117) used to deliver electrical stimulation to the target tissue (e.g., a peripheral nerve) of a patient. Once a distal portion 102 of the lead 100 is positioned around target tissue (e.g., a peripheral nerve 22) by, for example, folding distal portion 102 around peripheral nerve 22, a retracting loop 120 can protrude from lead body 110. In some embodiments, loop 120 can automatically protrude as lead body 110 is folded. Loop 120 can be used to fix distal portion 102 relative to the patient (e.g., by using a rivet, clip, and the like). When distal portion 102 is positioned around peripheral nerve 22, a gate 125 can be actuated and transitioned from a non-deployed state to the deployed state shown in FIG. 1B such that distal portion 102 and gate 125 completely surround a portion of peripheral nerve 22. When positioned as shown in FIG. 1B, anodes 116 and cathodes 117 can face centrally, toward peripheral nerve 22. Surrounding a target tissue (e.g., a nerve) and having centrally facing anodes 116 and cathodes 117 advantageously provides optimal capture of the target tissue (e.g., nerve) and helps to prevent the unintentional side capture of adjacent muscle tissue.

Figure 1C:
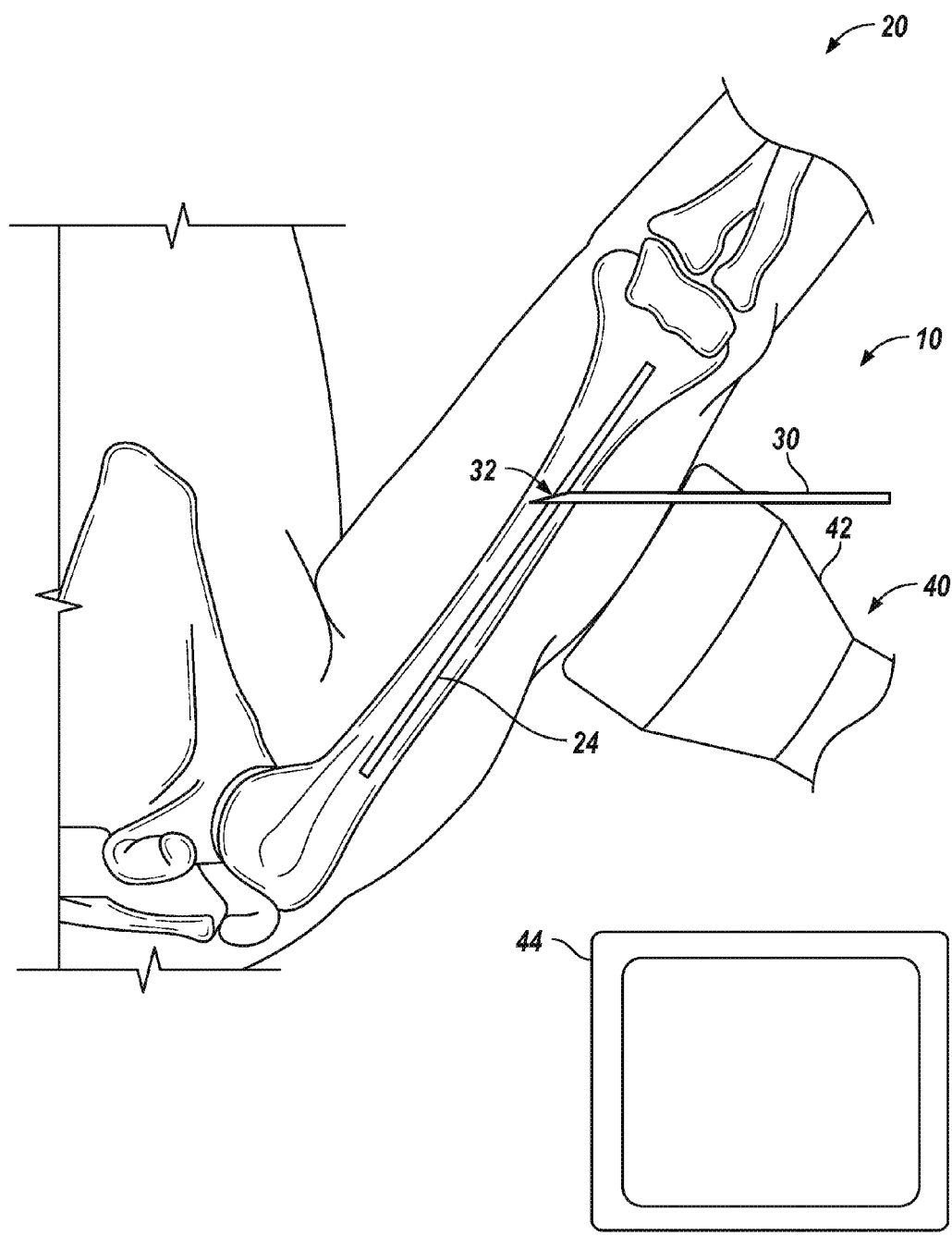

Referring now to FIGS. 1B-C, briefly, in use, an introducer needle 30 can be used to puncture the skin of a patient 20 and advanced toward any target tissue (e.g., extremity nerve), but shown as a radial nerve 24. The advancement of introducer needle 30 can be guided using an ultrasound imaging system 40 that includes an ultrasound probe 42 and a display 44. When needle 30 is located in a desired position, such as depicted in FIG. 1C, lead 100 can be advanced such that distal portion 102 of lead 100 extends beyond a tip 32 of needle 30. As lead 100 advances beyond tip 32, the distal portion transitions from a generally linear orientation inside the lumen of needle 30 to a curved orientation, depicted in FIG. 1B, partially surrounding a portion of radial nerve 24. In some embodiments, loop 120 can automatically protrude as lead body 110 extends beyond needle 30 and transitions to a curved orientation. Loop 120 can be used to fix distal portion 102 relative to the patient (e.g., by using a rivet, clip, and the like) and radial nerve 24. When distal portion 102 is positioned around radial nerve 24 (e.g., as distal portion 102 is positioned around peripheral nerve 22 in FIG. 1B), gate 125 can be actuated and transitioned from a non-deployed state to the deployed state shown in FIG. 1B such that distal portion 102 and gate 125 completely surround a portion of radial nerve 24. While the system described above uses a single port placement of lead 100, other techniques, such as a two-port placement described in connection with FIGS. 2A-D can be used to place lead 100.

Figure 2A:
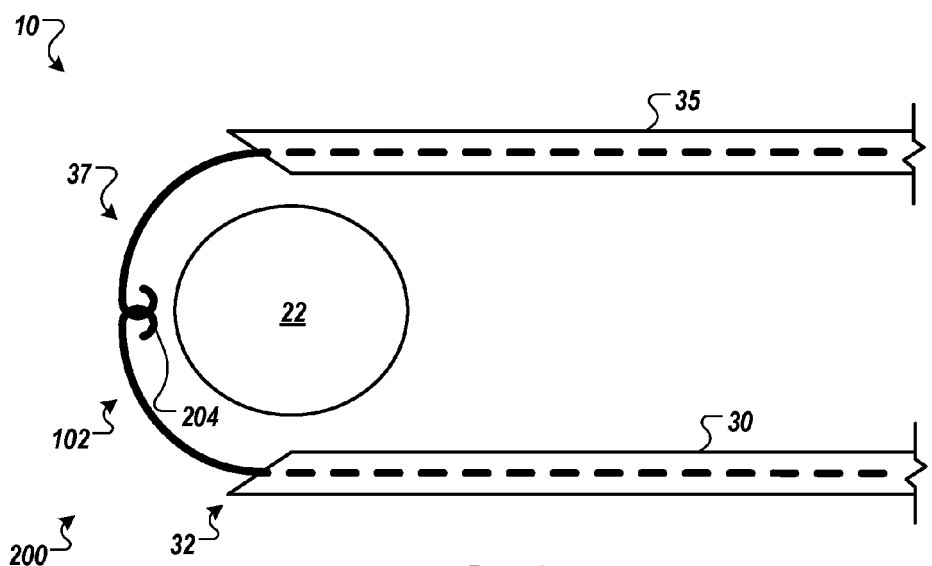
FIGS. 2A-D depict an electrode system for use in two-port placement, in accordance with some embodiments.
Figure 2B:
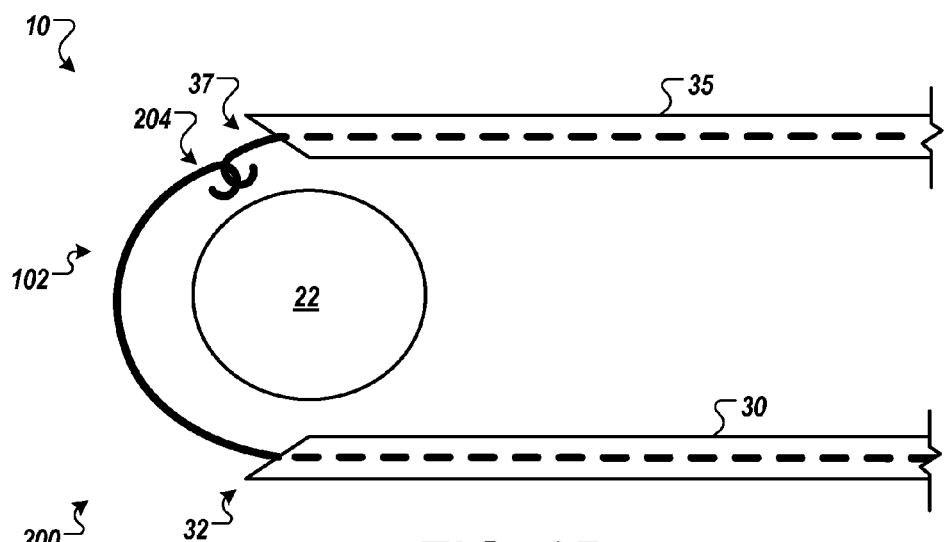
Figure 2C:
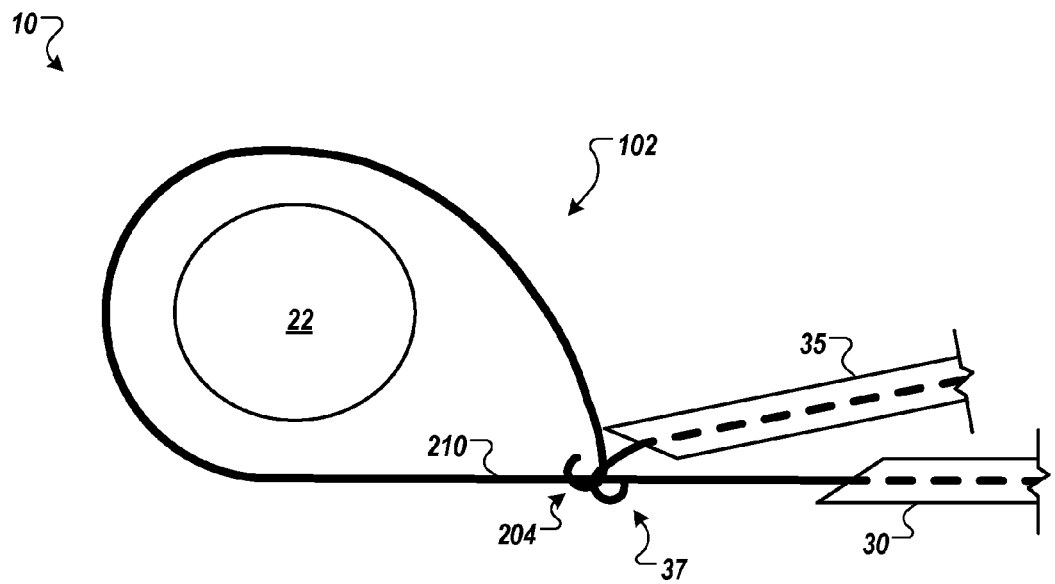

Referring now to FIGS. 2A-D, in some embodiments, electrode system 10 can include a flexible lead 200 that can be delivered through the interior lumen of a needle to a target tissue (e.g., a peripheral nerve) of a patient. Placement of lead 200, such that distal portion 102 of lead 200 surrounds a portion of the target tissue (e.g., peripheral nerve 22), can be facilitated through the use of a second needle. For example, as depicted in FIG. 2A, an introducer needle 30 can be used to puncture the skin of a patient and advanced toward peripheral nerve 22. As with the embodiment described in connection with FIG. 1C, the advancement of introducer needle 30 can be guided using an ultrasound imaging system. When needle 30 is located in a desired position, such as depicted in FIG. 2A, lead 200 can be advanced such that distal portion 102 of lead 200 extends beyond tip 32 of needle 30. As lead 200 advances beyond tip 32, distal portion 102 transitions from a generally linear orientation inside the lumen of needle 30 to a curved orientation, depicted in FIG. 2A, partially surrounding a portion of peripheral nerve 22.

Figure 2D:
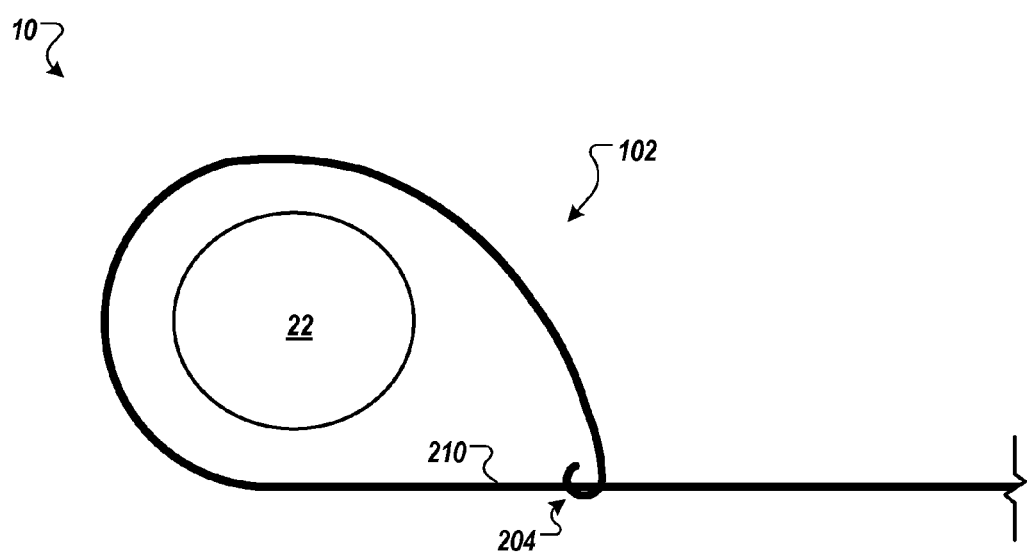

In some embodiments, a second needle 35 can be inserted into the patient and advanced (e.g., using ultrasound imaging for guidance) to a location depicted in FIG. 2A, on the opposite side of peripheral nerve 22. Once in a desired location, a grasper 37 can be deployed through the lumen of needle 35 until it reversibly couples with the distal tip portion of lead 200 (e.g., at a hook 204). Grasper 37 can be used to advance lead 200 around nerve 22 (see FIG. 2B) and couple a tip portion (e.g., hook 204) to a lead body 210 (see FIG. 2C), thus causing lead 200 to surround a portion of nerve 22. Referring to FIG. 2D, needles 30 and 35 can be removed.

Figure 3:
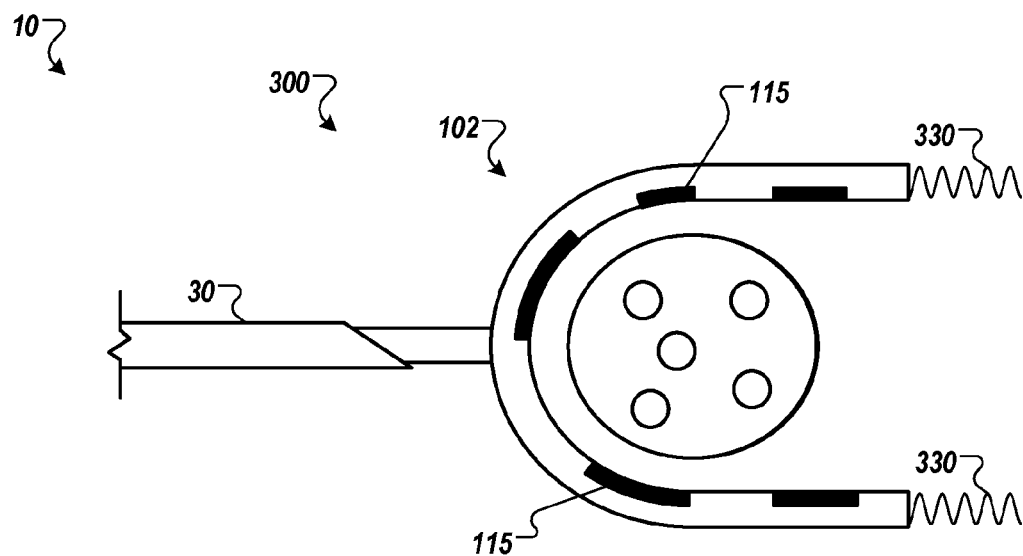
FIGS. 3-4 depict therapeutic leads, in accordance with some embodiments.
Figure 4:
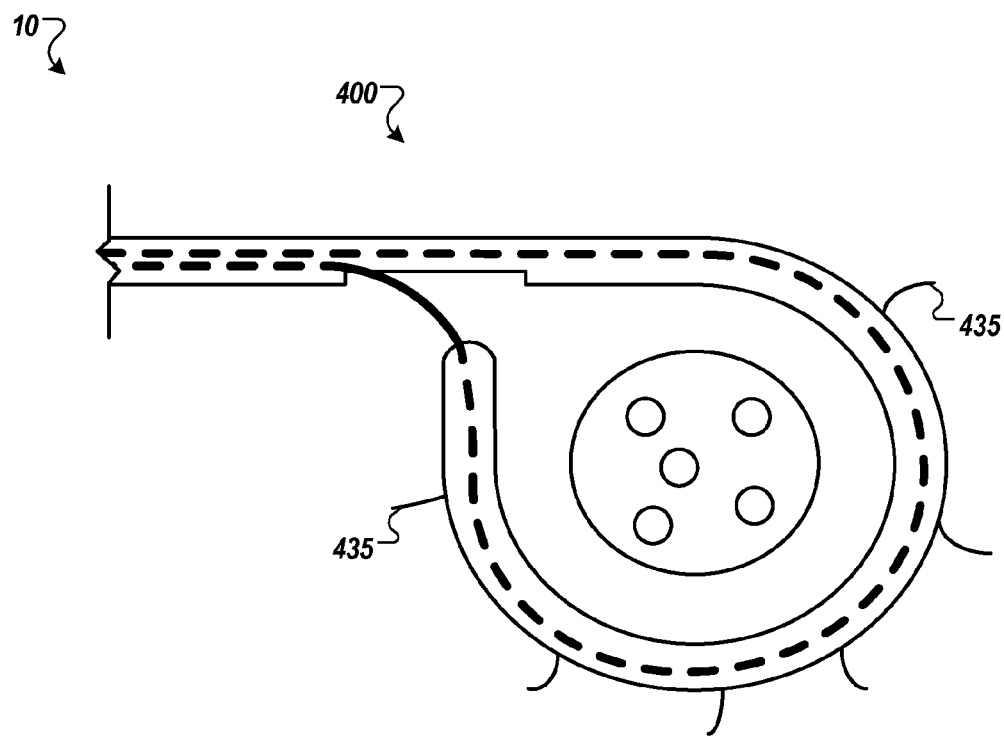

Referring now to FIGS. 3-4, in some cases, electrode system 10 can include features to simplify the deployment and anchoring of an electrode lead. For example, as depicted in FIG. 3, a lead 300 can include a shape memory alloy and can include a distal portion 102 that is generally U-shaped. As lead 300 is advanced from a needle 30, distal portion 102 can be allowed to transition to a U-shaped configuration and can be secured to surrounding tissue using anchors (e.g., helical anchors 330). In some cases, lead 300 can be secured, for example, using barbs, nails, and the like. As depicted in FIG. 4, a shape-memory or steerable lead 400 can be deployed through a single percutaneous port/introducer and can include tissue anchors 435 that can be either manually or automatically deployed.

Figure 5A:
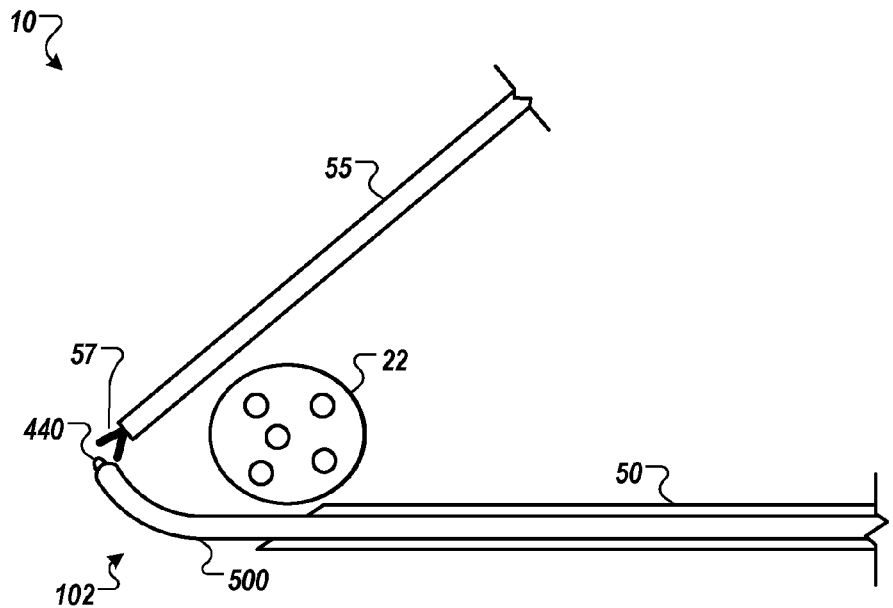
FIGS. 5A-C depict therapeutic leads, in accordance with some embodiments.
Figure 5B:
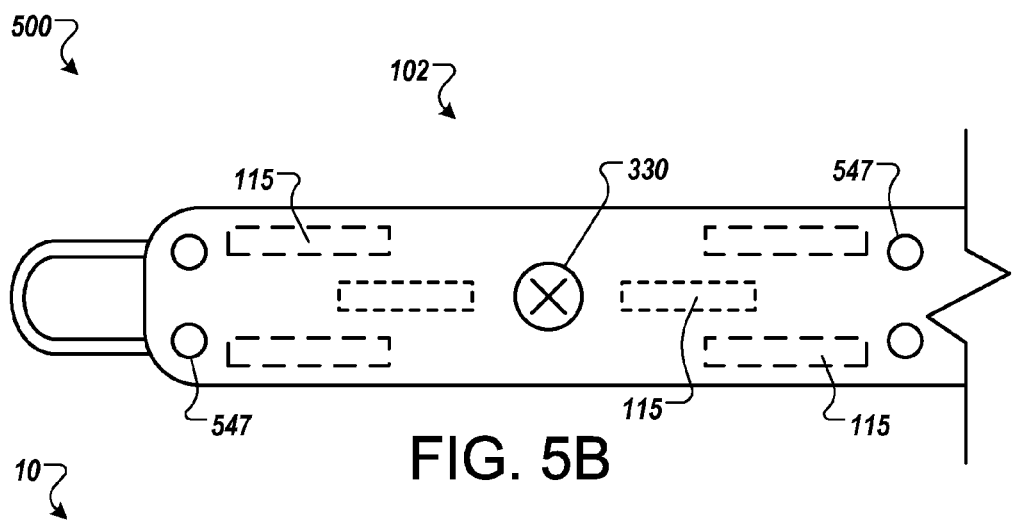
Figure 5C:
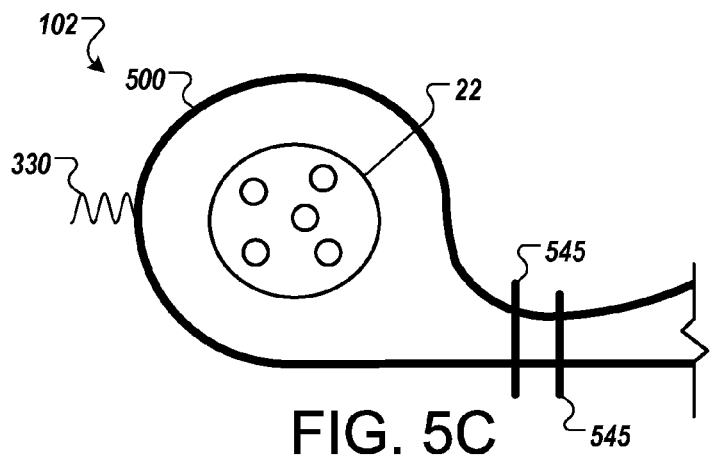

Referring now to FIGS. 5A-C, a curved or flexible lead 500 can be introduced via a delivery trocar 50 through one port of a two-port system. Delivery trocar 50 can be of any size or shape, including a flattened shape to accommodate paddle type electrodes. A second introducer 55 can be used to deploy a grasper 57, which can be used to grab the distal tip portion of lead 500 (e.g., at a hook, a loop 440, and the like) and pull it around nerve 22. The two ports can be aligned such that second introducer 55 is approximately parallel to first trocar 50 and in close proximity. Once distal portion 102 of lead 500 is pulled around nerve 22, anchor 330, one or more rivets 545 (e.g., through rivet openings 547), or any other attachment mechanism can be used to secure lead 500 onto itself, creating a circumferential placement around the nerve. Additional anchors, rivets or other securing mechanisms can optionally be used to stabilize the lead.

Figure 6:
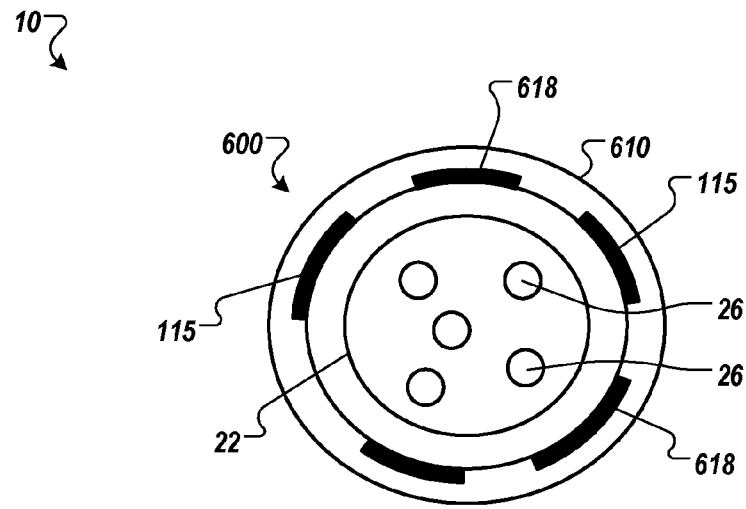
FIG. 6 depicts a therapeutic lead including multiple electrodes, in accordance with some embodiments.

Referring now to FIG. 6, an electrical lead 600 can include a lead body 610 with multiple electrodes 115. In some embodiments, electrodes 618 can be selectively modulated to capture the appropriate nerve elements 26 within nerve 22.

Figure 7:
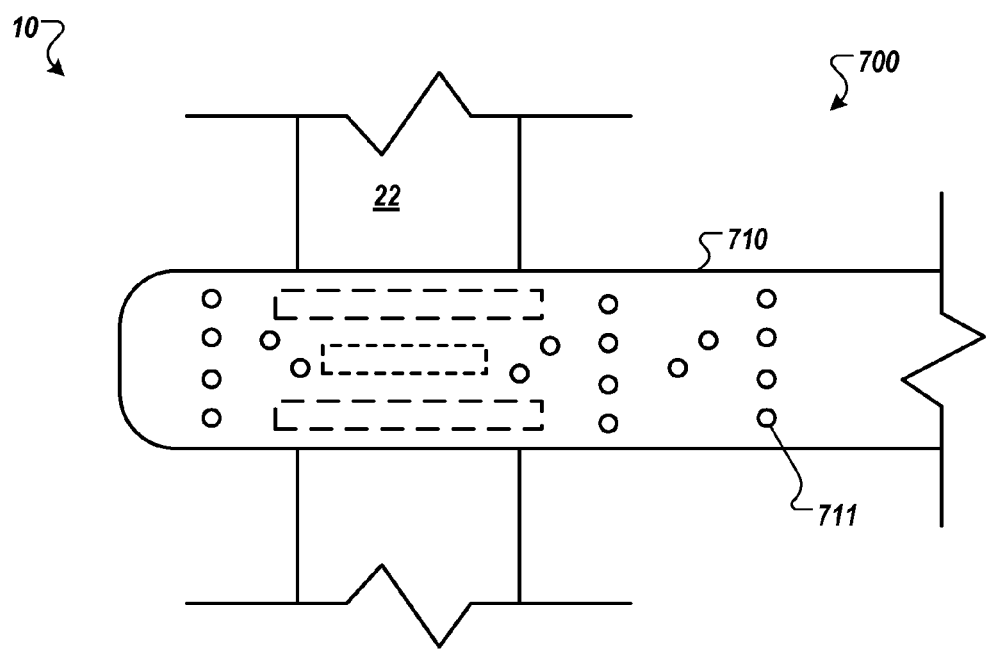
FIG. 7 depicts a therapeutic lead including drug eluting capability, in accordance with some embodiments.
Figure 10A:
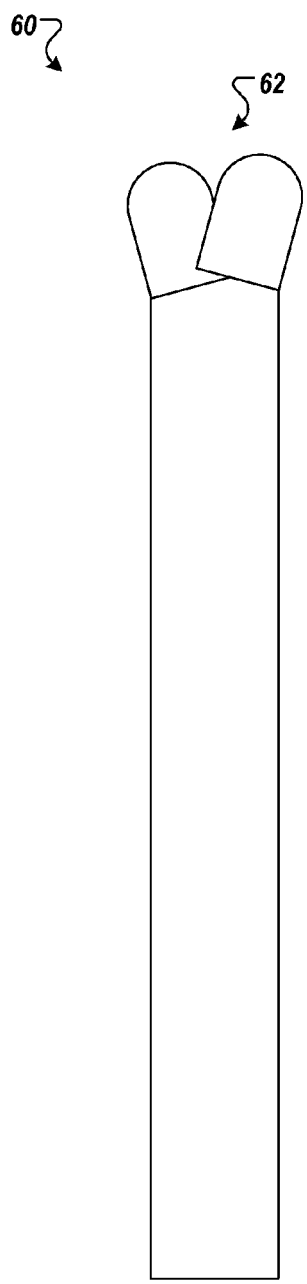
FIGS. 10A-D depict an electrode system including a tissue spreading tip, in accordance with some embodiments.
Figure 10B:
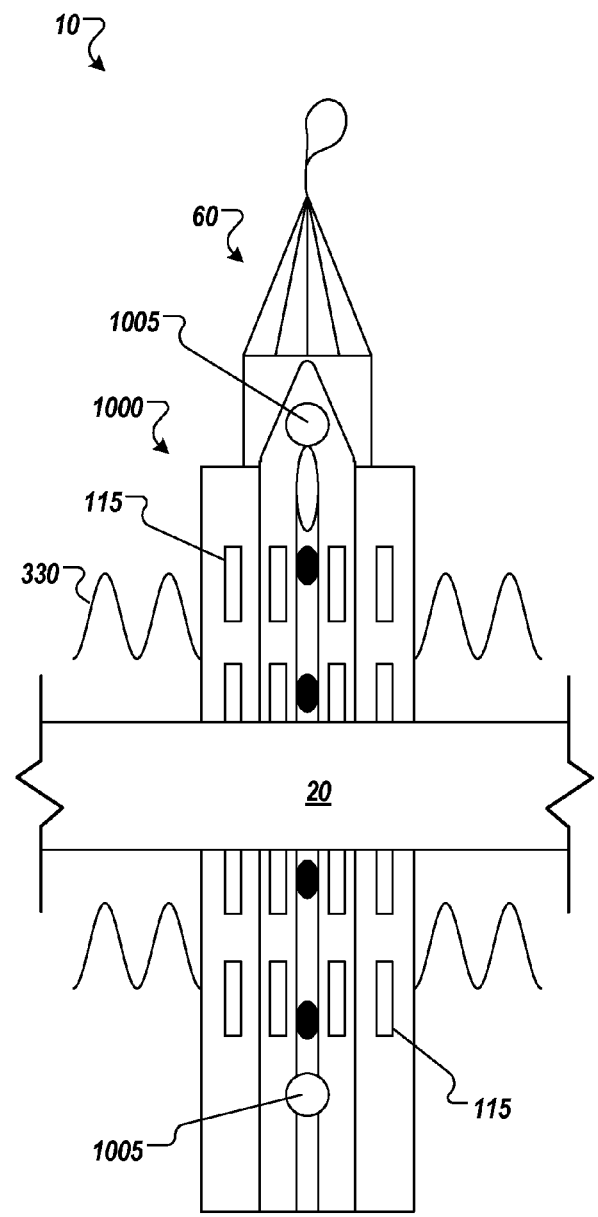
Figure 10C:
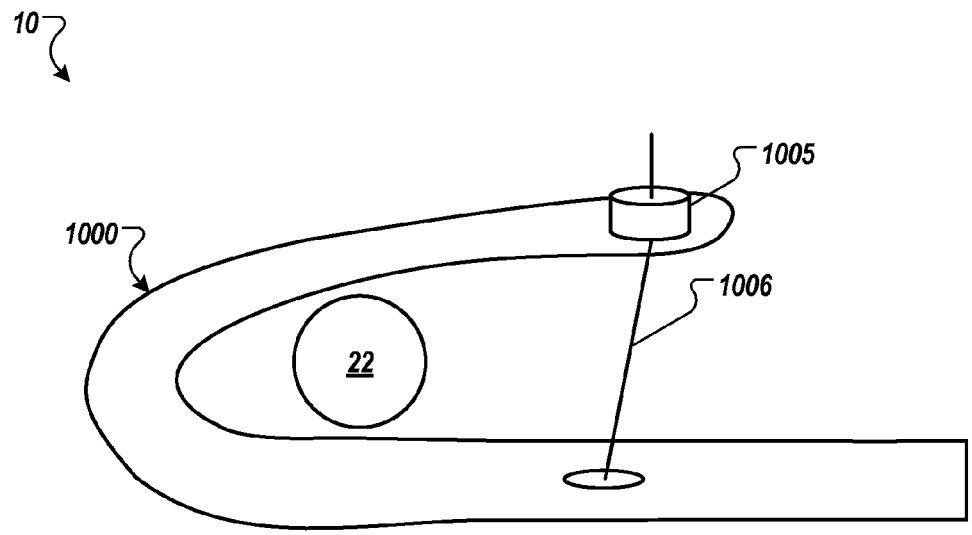
Figure 10D:
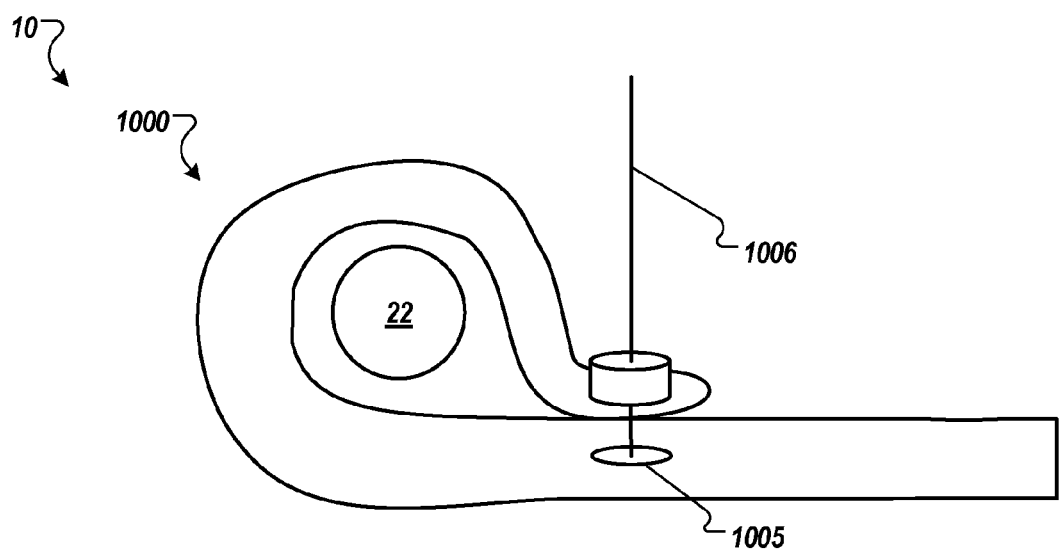

Referring now to FIG. 7, in some embodiments, an electrical lead 700 can include a lead body 710 with one or more ports 711, for example, to elute drugs, agents, or combinations of agents. Agents that can be eluted using lead 700 can include, without limitation, GABA (γ-aminobutyric acid) agonists (e.g., baclofen), anti-inflamatory agents (e.g., steroids), local anesthetics (e.g., lidocaine, bupivacaine, and the like), genetic material, vasodilators (e.g., nitric oxide, hydrolazine, and phentolamine), anti-fibrotic drugs (e.g., pirfenidone, gamma interferon, and colchicine), nerve growth factor inhibitors, calcitonin gene-related polypeptide antagonists, angiogenesis inhibitors, and alpha-2 agonists (e.g., clonidine). The agents may be stored in a fluid reservoir (not shown) of an implantable medical device control unit (not shown) and pumped or released to lead 700 as indicated. In some cases, an agent may be stored as a coating or other reservoir integral to the lead itself, in a separate fluid reservoir (external or internal), or the like.

Referring now to FIGS. 8A-B and 9A-B, in some cases, electrical leads 800 and 900 can include a shape-memory material such as nitinol. A sheath 60 may be positioned near a nerve 22, and lead 800 may be deployed from a distal tip portion 62 of sheath 60. For example, lead 800 can be advance beyond sheath 60, and sheath 60 can be retracted while lead 800 remains substantially fixed relative to nerve 22. As lead 800 deploys from sheath 60, an exposed distal portion 102 (including a shape-memory material) can transition from a substantially linear configuration (FIG. 8A) to a curved configuration, at least partially surrounding nerve 22 (FIG. 8B). In some embodiments, as depicted in FIGS. 9A-B, as lead 900 is deployed from sheath 60, an exposed distal portion 102 of lead 900 can curve or fold along a longitudinal line, at least partially surrounding nerve 22 as shown in FIG. 9B.

Referring now to FIGS. 10A-D, tissue spreading or tunneling devices may be included in an electrode system 10 to aid in the advancement of an electrical lead. For example, a sheath 60 can include a tissue spreading tip 62. An electrode lead 1000 can be passed over sheath 60. After wrapping target tissue (e.g., nerve 22), lead 1000 can be secured using fixation devices 1005 and 1006.

Figure 11A:
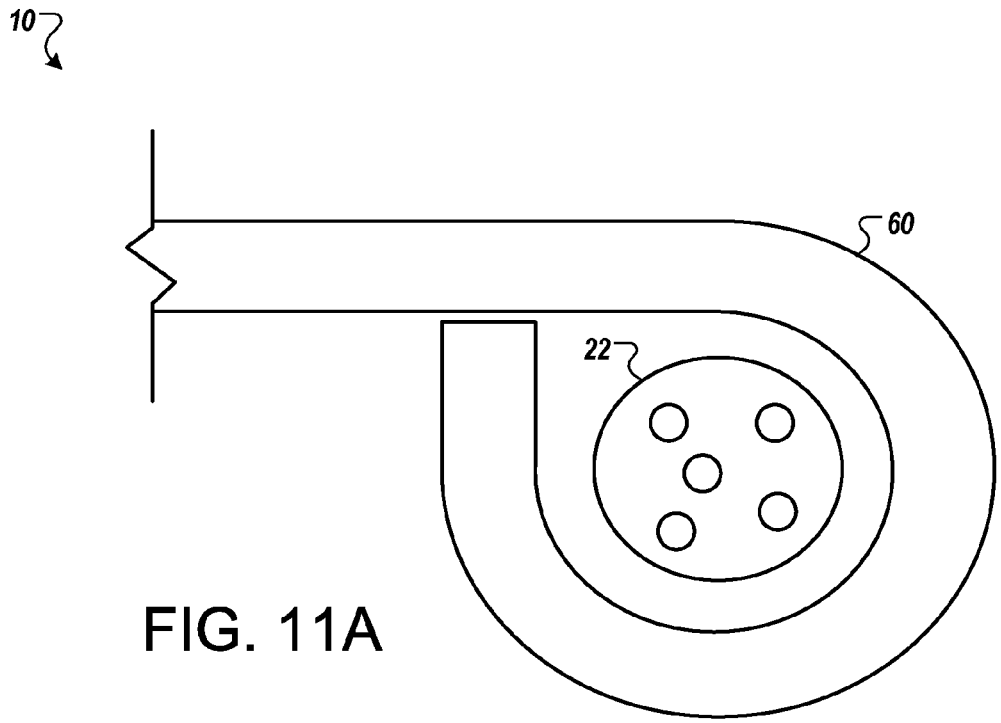
FIGS. 11A-E depict an electrode system including a steerable sheath, in accordance with some embodiments.
Figure 11B:
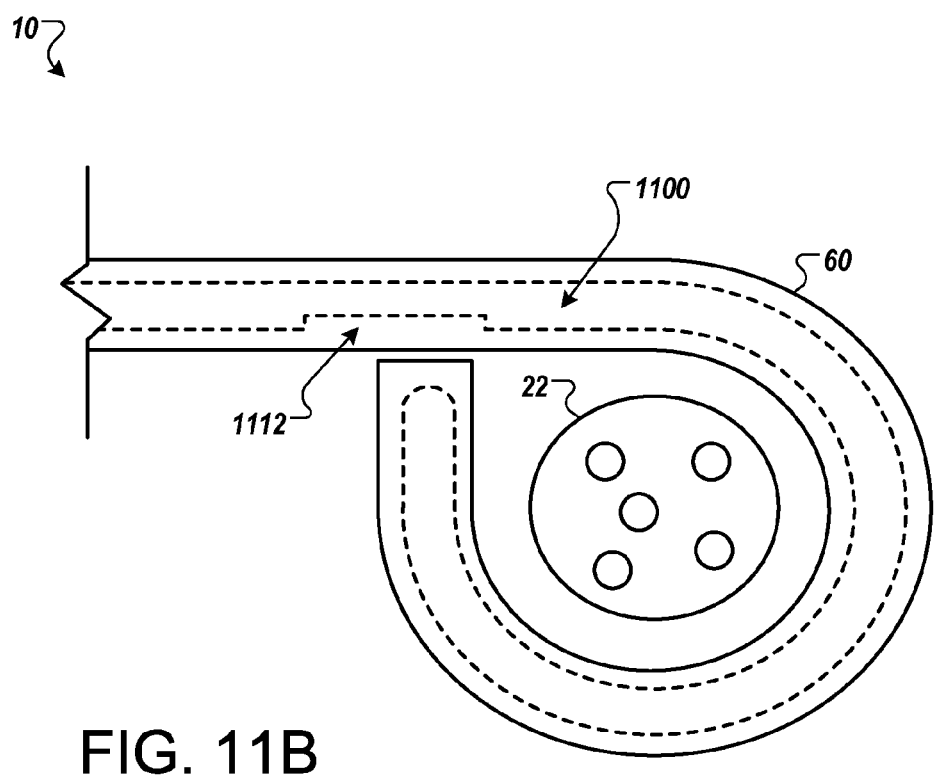
Figure 11C:
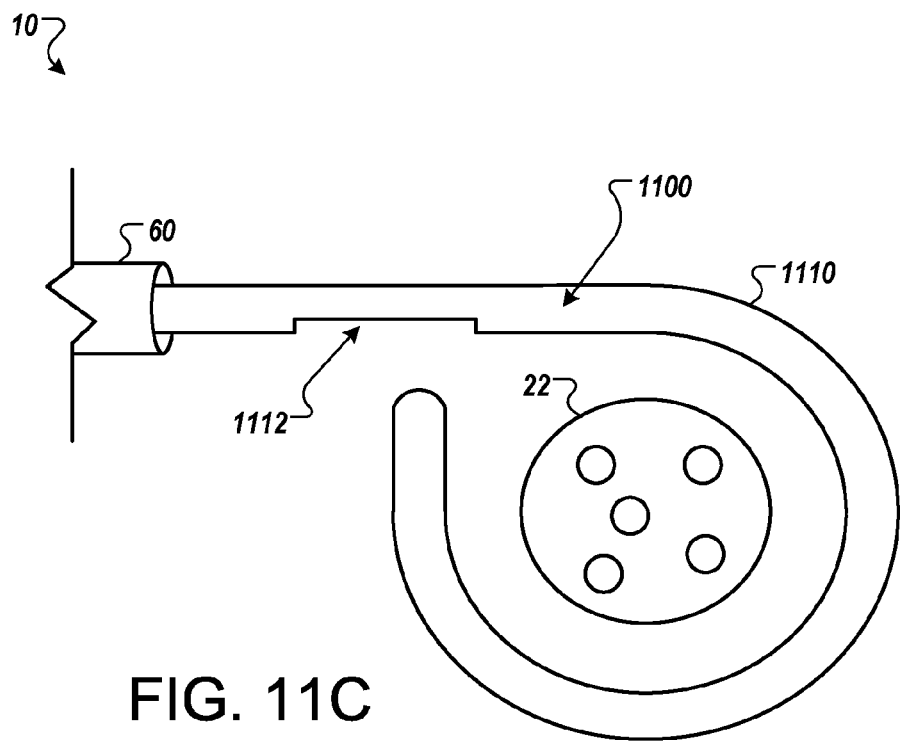
Figure 11D:
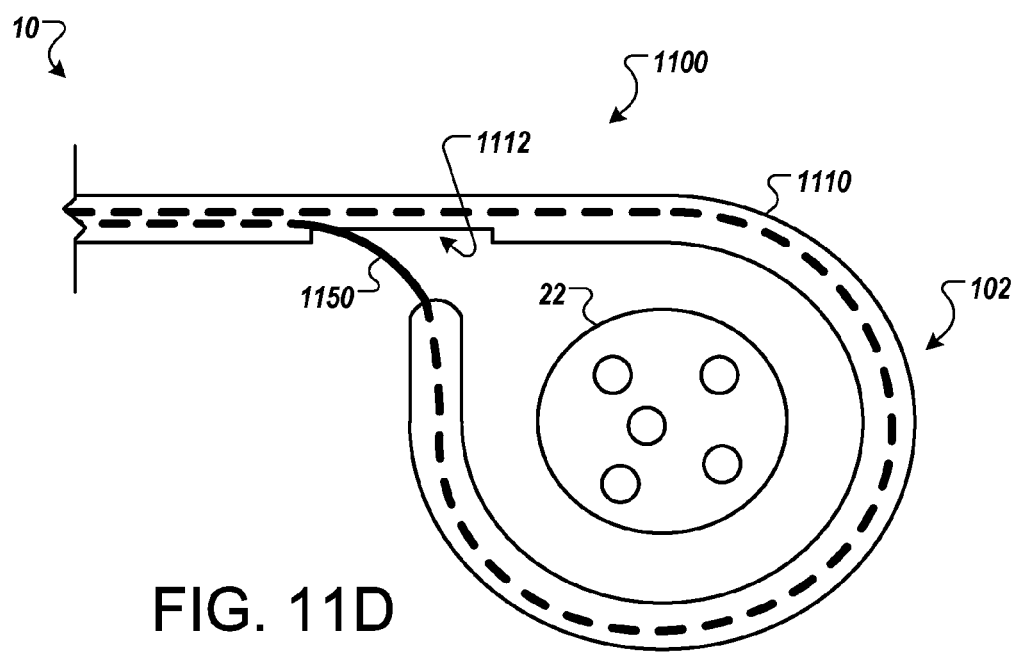
Figure 11E:
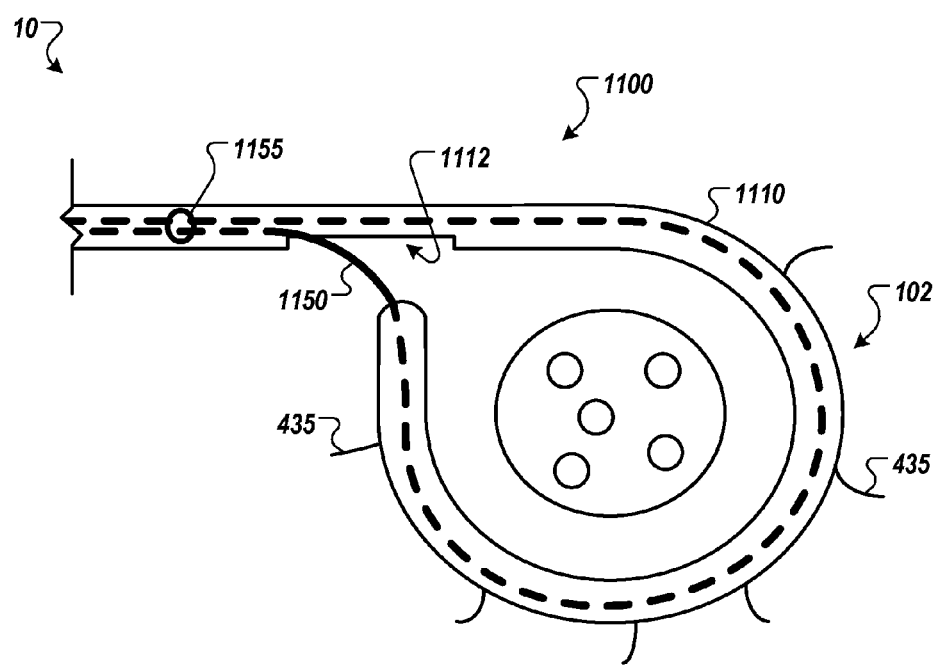

Referring now to FIGS. 11A-E, a steerable sheath 60 can optionally include a dissecting tip that may be deployed to encircle a target tissue (e.g., nerve 22). Steerable sheath 60 may also optionally include a wire or stylet (not shown) to enhance stiffness or tissue dissection. Once steerable sheath 60 has encircled nerve 22, an electrical lead 1100 can be deployed through the lumen of sheath 60 (FIG. 11B). Lead 1100 can include a notch 1112 in an outer wall of a lead body 1110 that can provide access to a hollow lumen of lead 1100. Notch 1112 may be demarcated, for example, by echogenic markers, markers visible by fluoroscopy, and the like. As depicted in FIG. 11C, sheath 60 may be refracted or removed (e.g., via a peel-away design) to expose lead 1100 in the lumen of sheath 60. Lead 1100 can include features that provide a larger platform for an electrode array included in lead body 1110. For example, lead body 1110 can be designed to unfold or unfurl, thus exposing more surface area to nerve 22 surrounded by lead 1100. In some embodiments, a wire 1150 can be passed through the lumen of lead 1100, around nerve 22, and through notch 1112 in the outer wall of lead body 1110, thus completing a loop around nerve 22 (FIG. 11D). Wire 1150 can continue to be advanced, for example, until it extends beyond the proximal end (not shown) of lead 1100. At this point, wire 1150 can be pulled to tighten a distal portion 102 of lead 1100 to substantially surround nerve 22. As depicted in FIG. 11E, lead 1100 can be secured to maintain distal portion 102 substantially surrounding nerve 22. In some embodiments, wire 1150 can be secured (e.g., using locking clips 1155) to maintain distal portion 102 in a desired configuration. In some embodiments, the distal portion can be secured using fasteners, anchors, and the like.

Figure 12A:
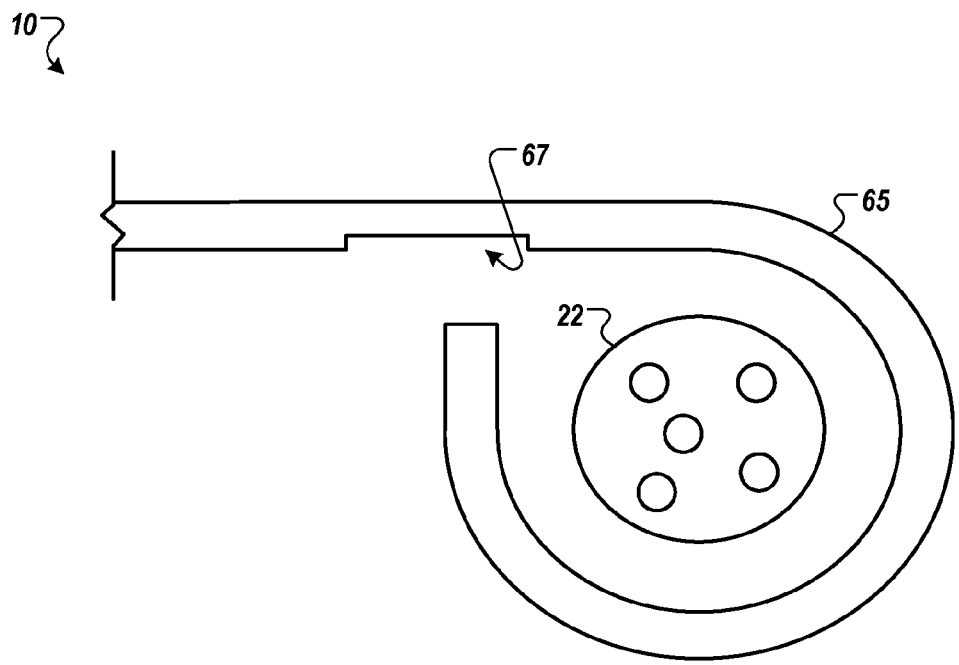
FIGS. 12A-D depict an electrode system including a steerable sheath, in accordance with some embodiments.
Figure 12B:
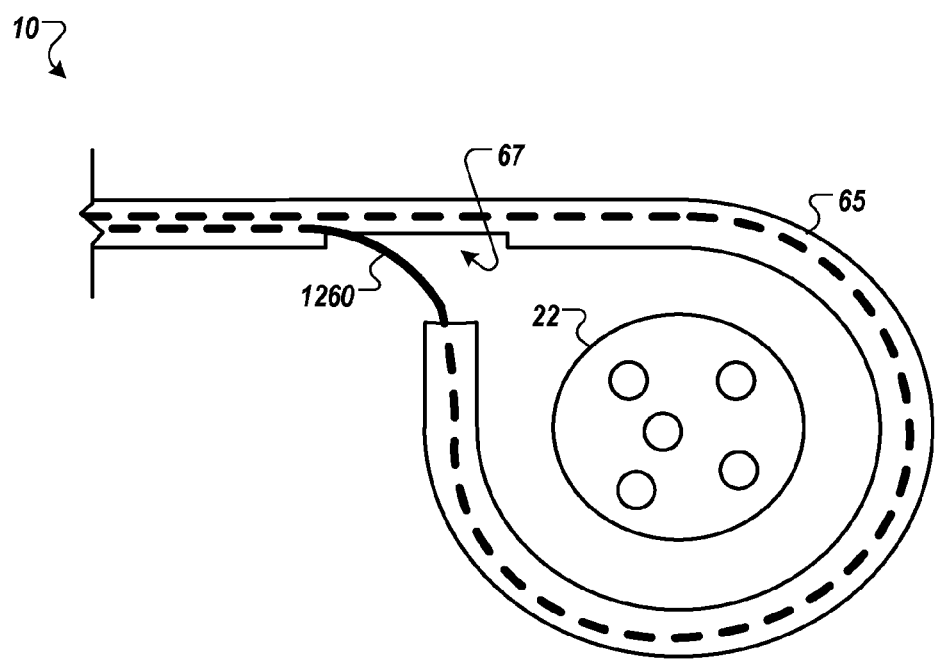
Figure 12C:
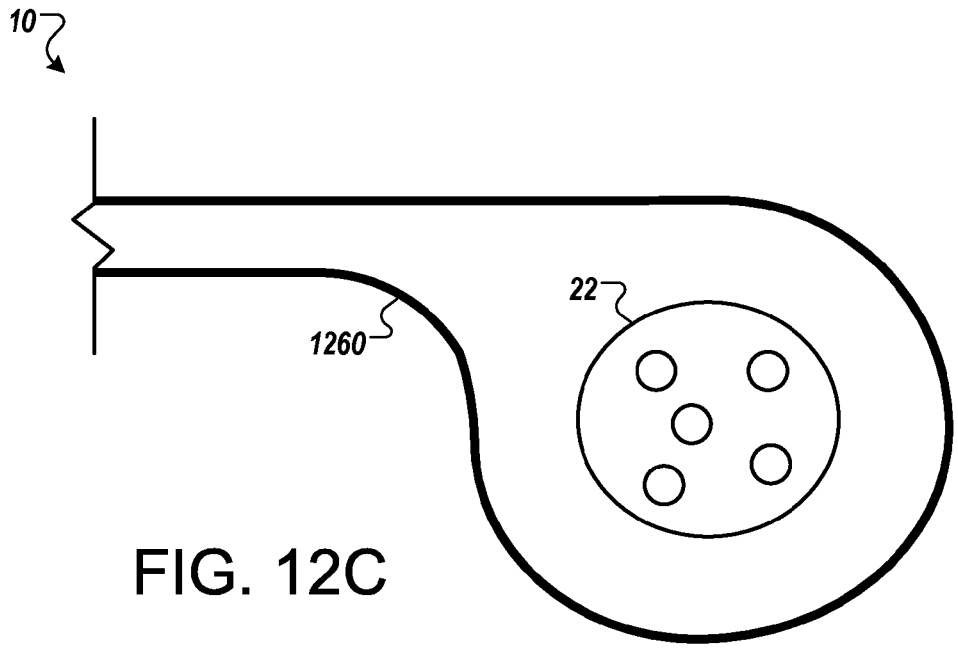
Figure 12D:
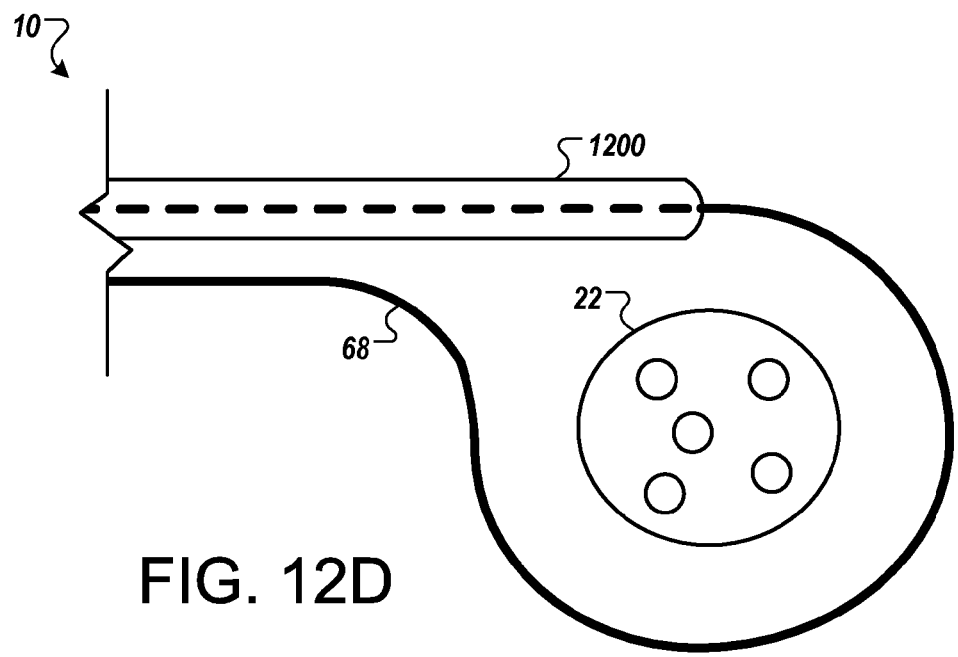

Referring now to FIGS. 12A-D, a notched steerable sheath 65 can be advanced to a target tissue (e.g., a nerve 22). A dissection stylet (not shown) or dissecting sheath tip (not shown) may aid in the deployment of sheath 65. A notch 67 can provide an access opening to the lumen of sheath 65. Once steerable sheath 65 advances around nerve 22, a wire 1260 may be passed through the lumen of sheath 65, fed through notch 67, and advanced to a proximal access port (not shown), as shown in FIG. 12B. Referring to FIG. 12C, sheath 65 may then be removed (e.g., by a peel-away mechanism, a tear-away mechanism, and the like). Referring to FIG. 12D, a lead 1200 can be advanced over a wire 1260 to and around nerve 22. When in a desired location, lead 1200 can be secured in place, for example, by advancing a locking clip, another lead, a wire securing device, anchors, and the like.

Figure 13A:
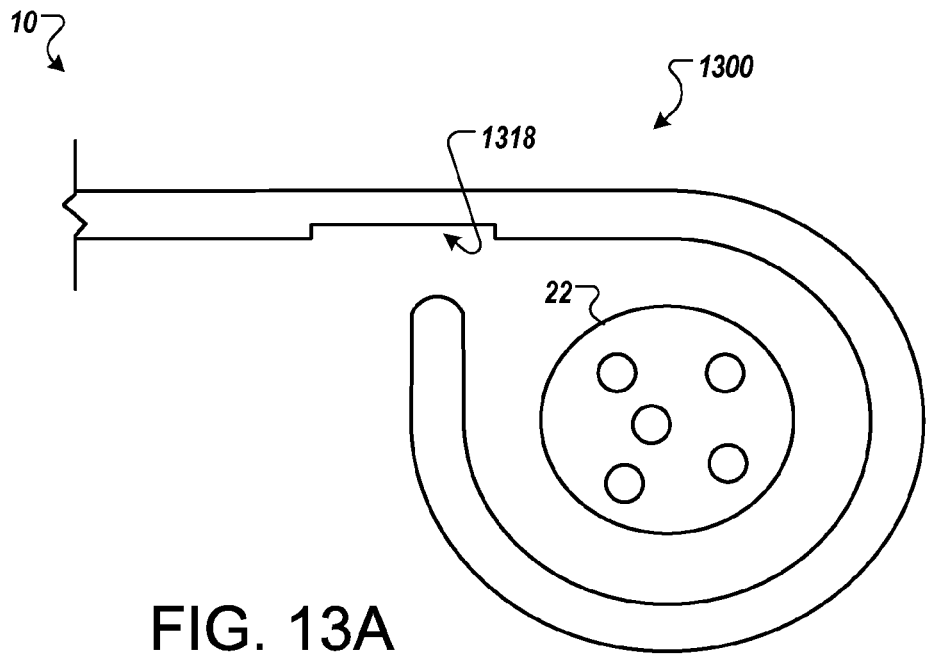
FIGS. 13A-C depict an electrode system including a steerable electrode, in accordance with some embodiments.
Figure 13B:
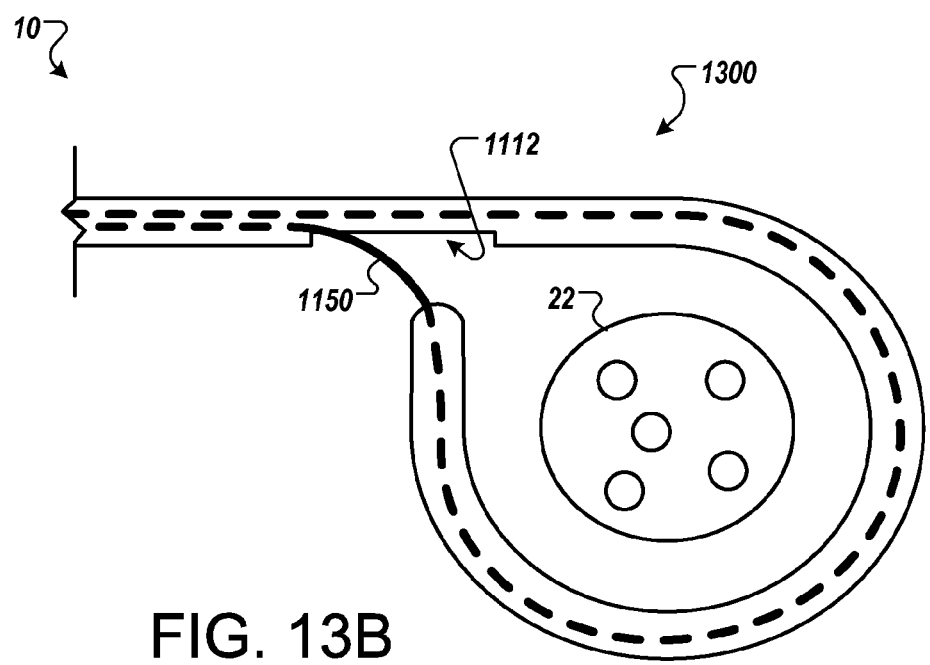
Figure 13C:
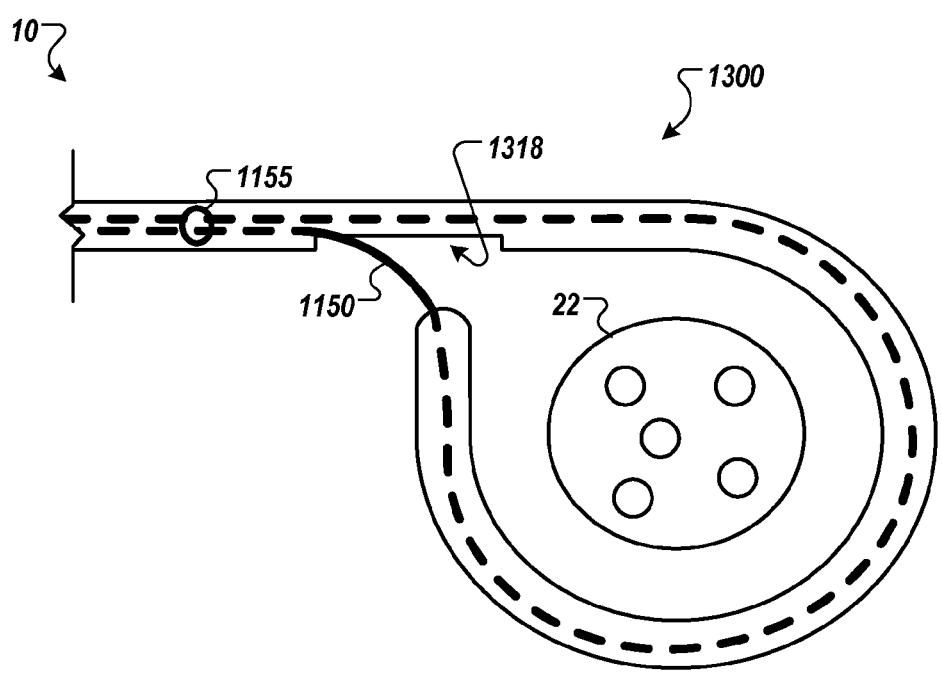

Referring now to FIGS. 13A-B, a steerable lead 1300 can include the notch 1112 that allows access to the lumen of lead 1300. Lead 1300 may be advanced toward a target tissue (e.g., nerve 22). Once steerable lead 1300 has substantially circumnavigated nerve 22, a wire 1150 can be passed though the lumen of lead 1300, fed through notch 1112, and advanced through the lumen of lead 1300 to a proximal access port (not shown). Lead 1300 can be secured, for example, using locking clips 1155, a securing device, an anchoring mechanism, and the like.

Figure 14:
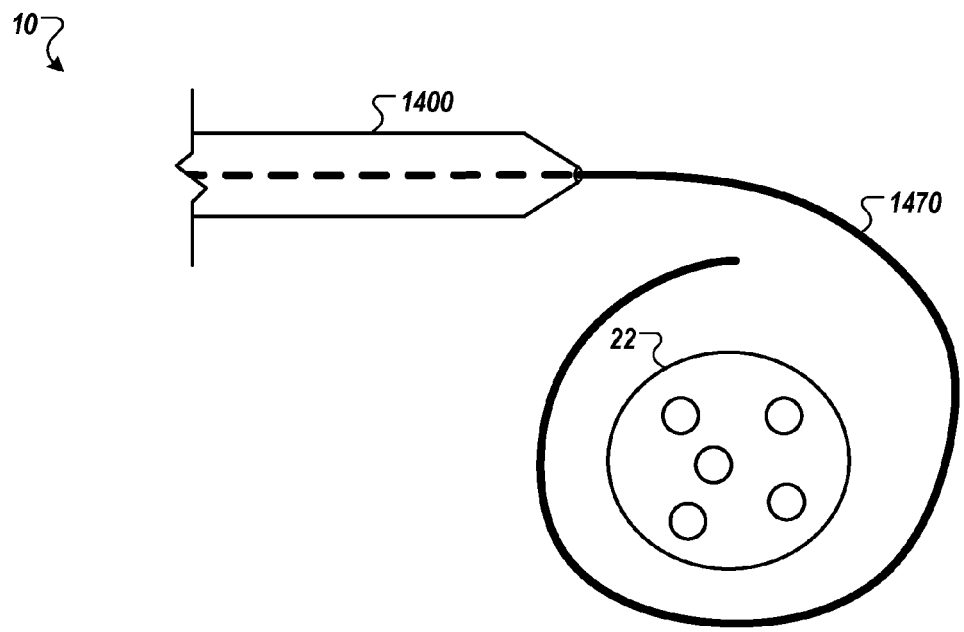
FIG. 14 depicts an electrode system including an electrode lead that is advanceable over a shape-memory wire.

Referring now to FIG. 14, a wire 1470 (e.g., a nitinol wire 1470) can be passed (e.g., through a needle, a sheath, a lead 1400, and the like) to a target tissue (e.g., nerve 22). Wire 1470 can be advanced to wrap around nerve 22. Lead 1400 can be advanced over wire 1470, wrapping nerve 22. In some embodiments, wire 1470 can be shaped to include different diameter curves in which the radius of curvature can be based, at least in part, on the diameter of the target tissue (e.g., nerve 22) to be wrapped (e.g. the ulnar nerve, the tibial nerve, the sciatic nerve, and vascular structures such as an artery).

Figure 15:
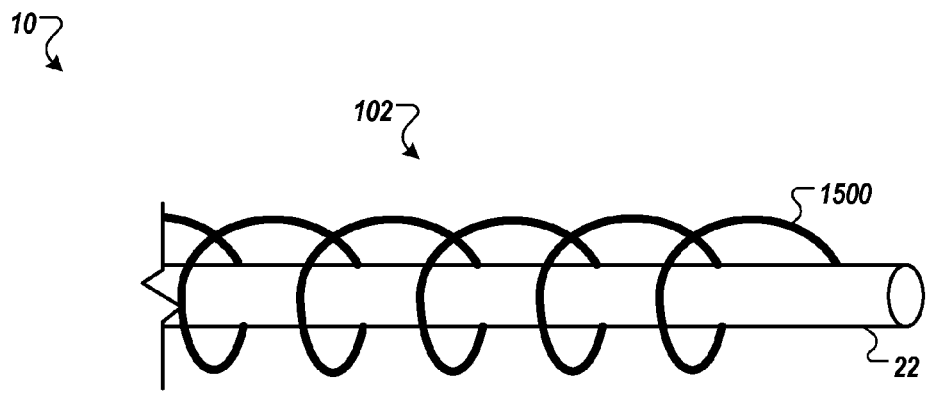
FIG. 15 depicts an electrode system including a lead that corkscrews longitudinally around a tissue (e.g., a nerve).

Referring now to FIG. 15, an electrical lead 1500 can be configured such that a proximal portion 102 of lead 1500 can corkscrew longitudinally around a target tissue (e.g., nerve 22).

Figure 20:
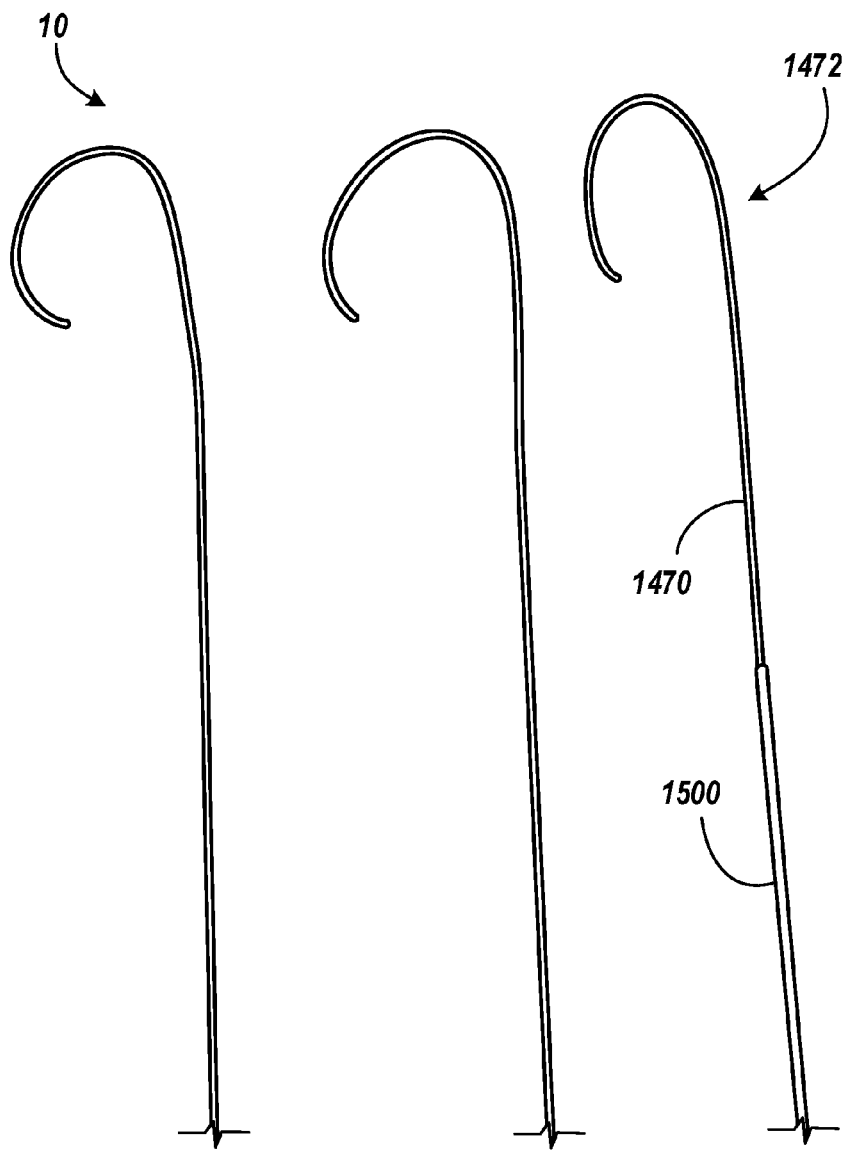
FIG. 20 depicts the loop ends of various lead wires, in accordance with some embodiments.
Figure 21:
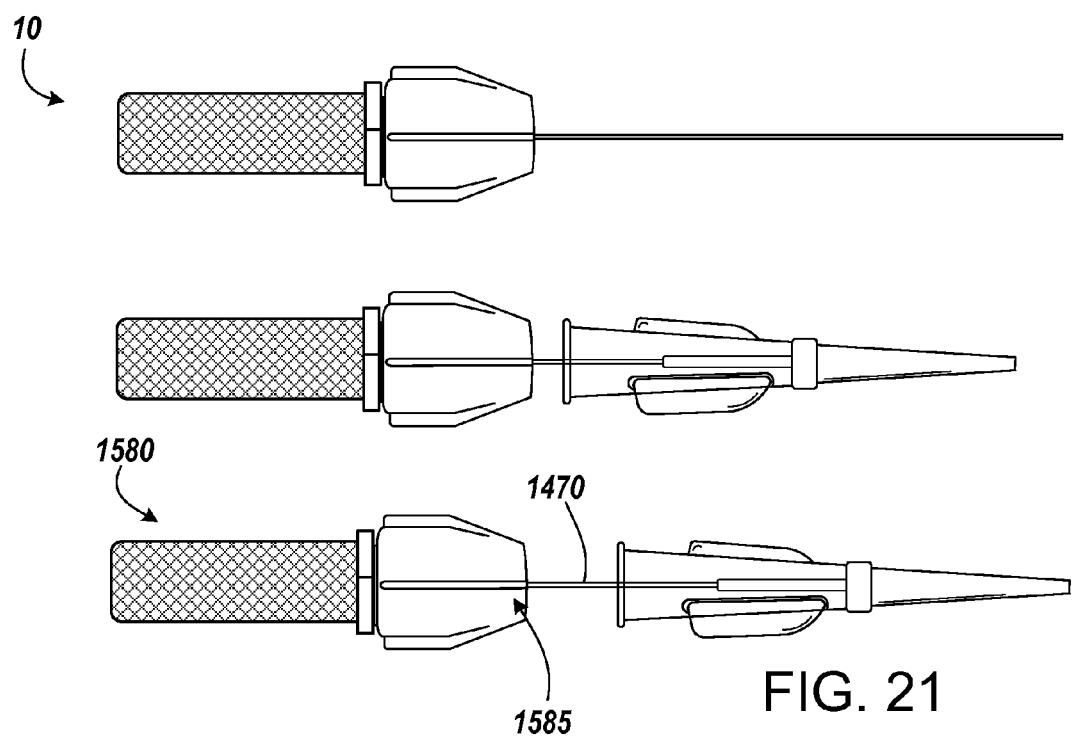
FIG. 21 depicts the proximal ends of various electrode systems, in accordance with some embodiments.
Figure 23A:
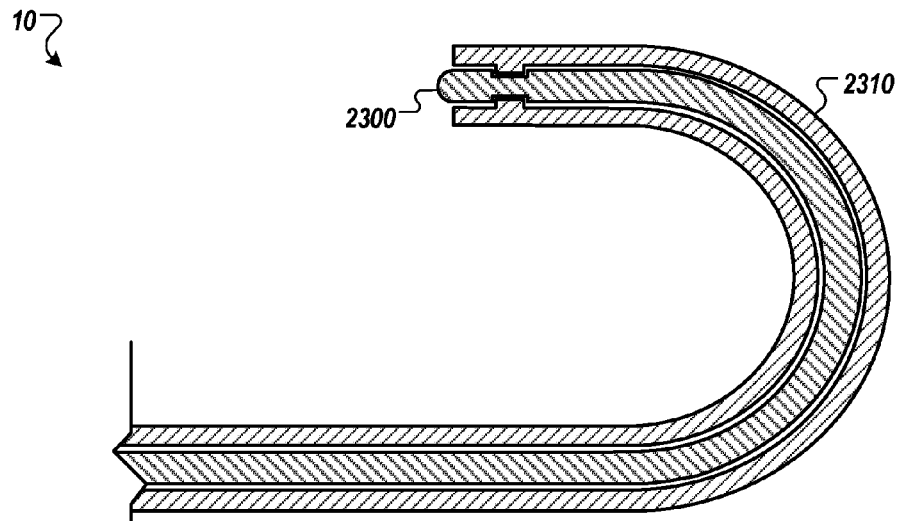
FIGS. 23A-D depict electrode systems, including features to reduce lead travel, in accordance with some embodiments.
Figure 23B:
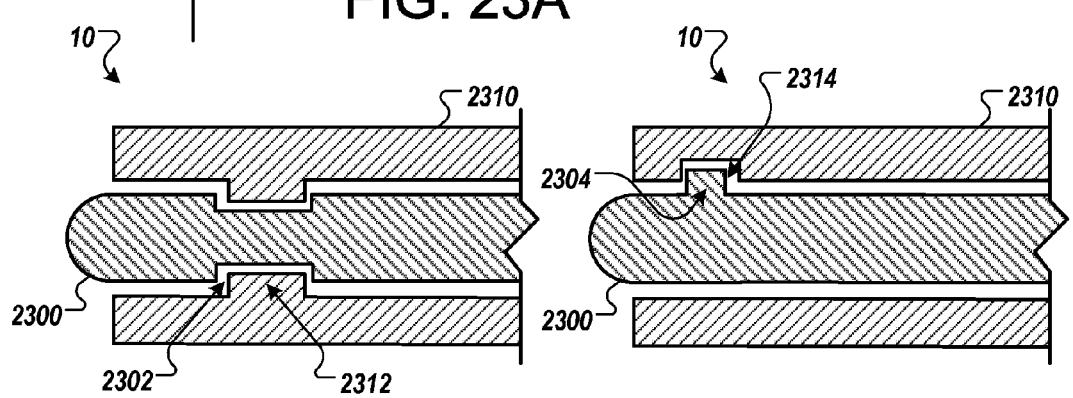
Figure 23C:
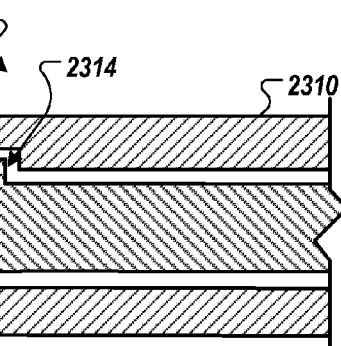
Figure 23D:
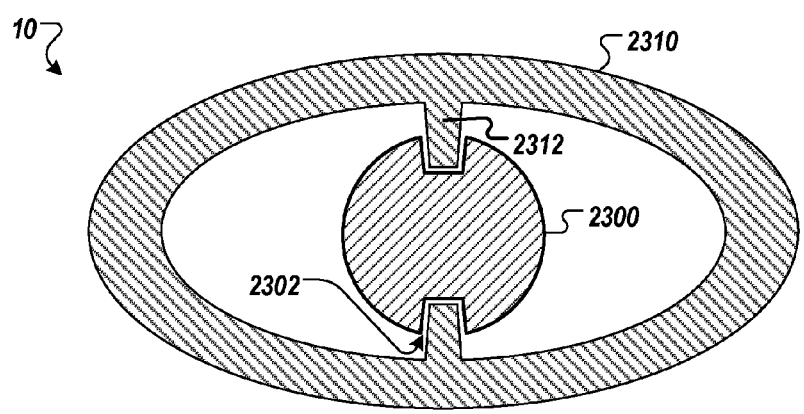

Referring now to FIGS. 20-21, a wire 1470 (e.g., a nitinol wire) can be passed (e.g., through a needle, a sheath, a lead 1500, and the like) to a target tissue (e.g., a nerve). The orientation of a loop 1472 on the end of wire 1470 can be controlled by a gripable handle 1580 included on the proximal end of an electrode system 10. The orientation of loop 1472 can be indicated by an indicator marking 1585 on or near handle 1580.

Referring now to FIGS. 22A-D, in some embodiments, an electrode system 10 can include features to reduce or eliminate lead travel after deployment. For example, a wire 2200 can include a bead 2202, a stop 2204 located proximal to the distal end, a diamond or arrow shaped end 2206, a flared end 2208, or the like. The size of these features in FIGS. 22A-D may be exaggerated for clarity.

Referring now to FIGS. 23A-D, in some embodiments, an electrode system 10 can include features to reduce or eliminate lead travel after deployment. For example, a wire 2300 can include one or more notches 2302 that can mate with corresponding protrusions 2312 in a lead 2310. In some embodiments, wire 2300 can include one or more protrusions 2304 that can mate with corresponding notches 2314 in lead 2310.

Figure 24A:
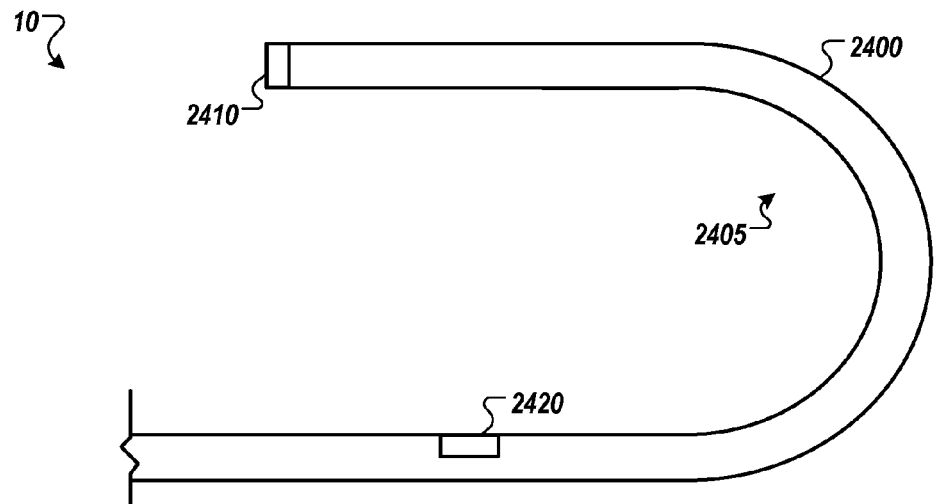
FIGS. 24A-C depict electrode systems, including features to assist in lead placement and loop closing, in accordance with some embodiments.
Figure 24B:
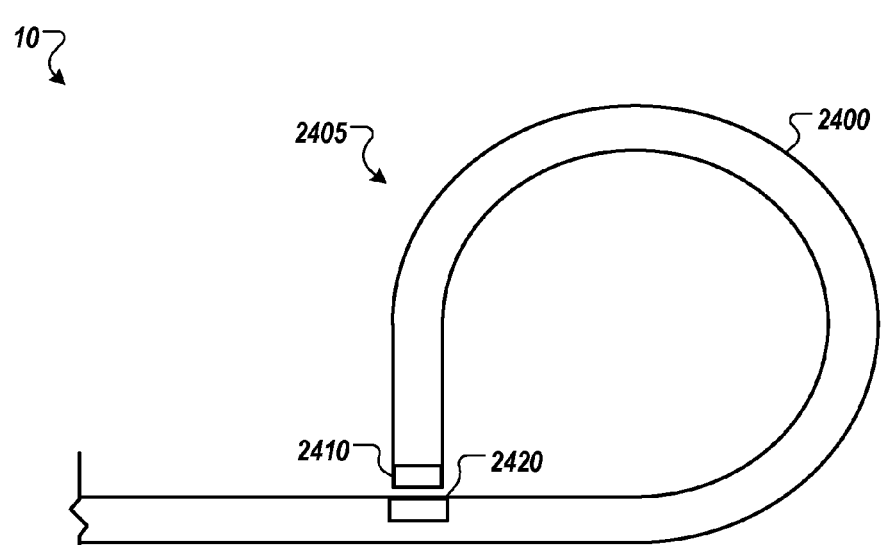

Referring now to FIGS. 24A-B, an electrode system 10 can include features to assist in closing a lead loop. For example, a wire 2400 can include one or more magnets 2410 in the distal end and one or more magnets 2420 along a shaft of wire 2400. The magnets can be brought into close proximity, as depicted in FIG. 24B, such that magnets 2410 and 2420 attract each other and assist in closing a loop portion 2405 in wire 2400.

In some embodiments, other methods can be employed to assist in closing loop portion 2405. For example, bioadhesives, epoxy, glue, and the like can be used. In some embodiments, magnets 2420 can be included in a delivery sheath, an electrode lead, and the like.

Figure 24C:
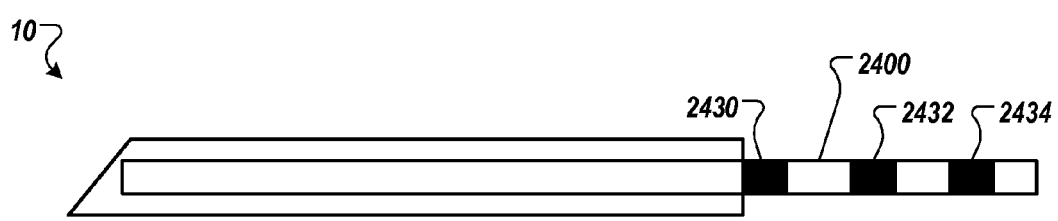
Figure 25A:
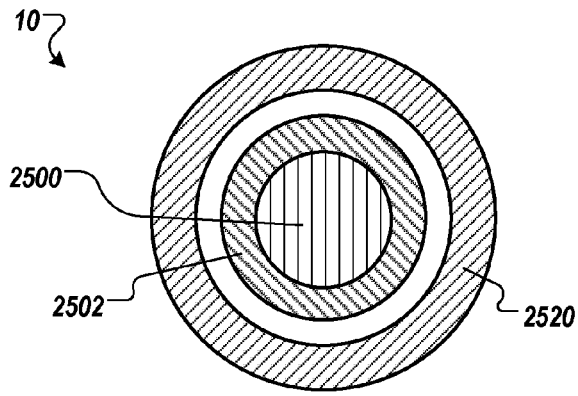
FIGS. 25A-C depict electrode systems, including features to reduce lead travel, in accordance with some embodiments.
Figure 25B:
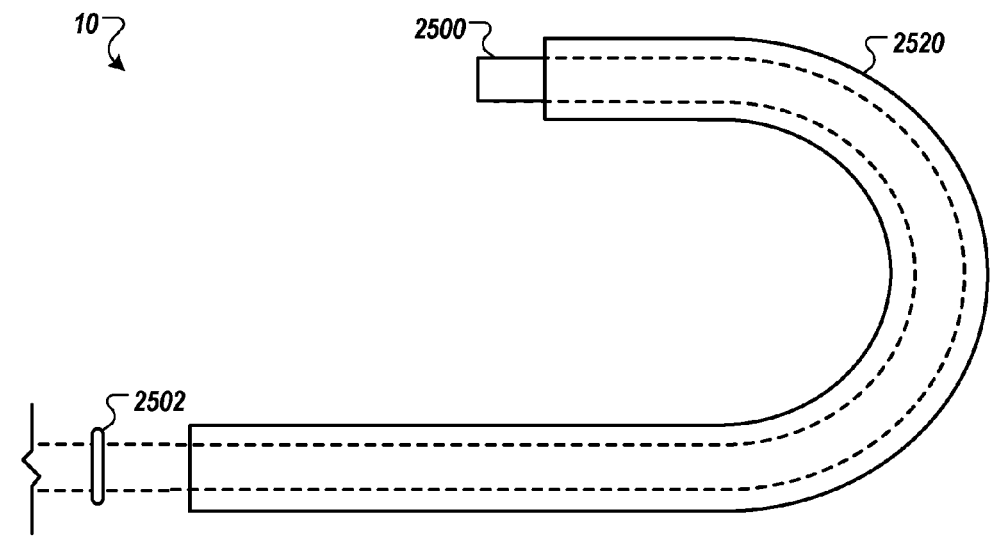
Figure 25C:
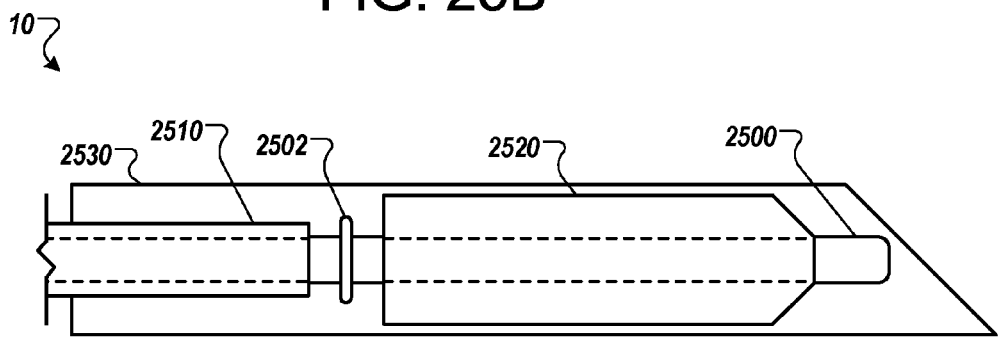
Figure 26A:
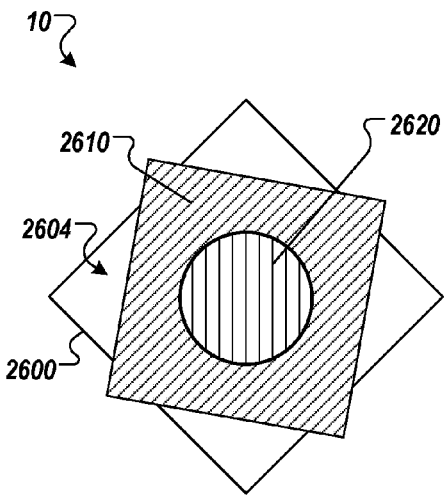
FIGS. 26A-C depict electrode systems, including anchors to reduce lead travel and anchor deployment systems, in accordance with some embodiments.
Figure 26B:
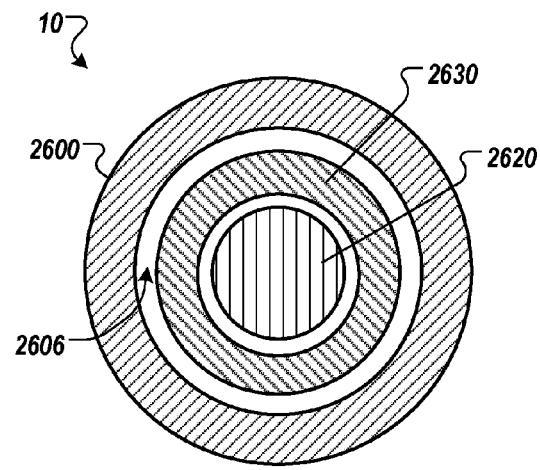
Figure 26C:
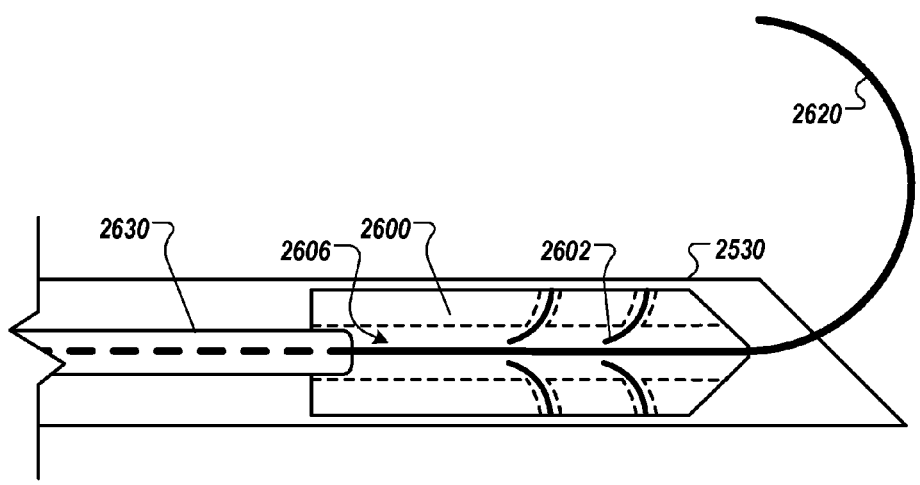

Referring now to FIG. 24C, an electrode system 10 can include features that allow a user to determine the deployment status of a wire 2400. For example, wire 2400 can include one or more indicators, such as indicator markings 2430, 2432, and 2434 indicating no deployment, partial deployment, or full deployment, respectively. In some embodiments, wire 2400 can include more or less indicator markings.

Referring now to FIGS. 25A-C, 26A-C, and 27A-B, in some embodiments, an electrode system 10 can include features to reduce or eliminate lead travel after deployment. For example, a wire 2500 can include one or more locking elements 2502. Locking element 2502 can be located distal to and advanced by a pusher 2510 and proximal to a lead 2520.

Wire 2500, locking elements 2502, pusher 2510, lead 2520, and the like can be deployed from within a needle 2530.

In some embodiments, an electrode system can include anchors 2602 in a lead paddle 2600 that can be deployed from the proximal end of electrode system 10. For example, electrode system 10 can include a square design wherein a lumen 2604 of lead paddle 2600 and a hollow pusher 2610 (through which a wire 2620 can pass) have generally square-shaped cross-sections. Anchors 2602 can be transitioned from a non-deployed state, as depicted in FIG. 27A, to a deployed state, as depicted in FIG. 27B, by rotating pusher 2610 relative to lead paddle 2600. In another example, an electrode system 10 can include a round design wherein a lumen 2606 of lead paddle 2600 and a hollow pusher 2630 (through which a wire 2620 can pass) have generally round-shaped cross-sections. Anchors 2602 can be transitioned from a non-deployed state, as depicted in FIG. 27A, to a deployed state, as depicted in FIG. 27B, by advancing pusher 2630 into lumen 2606 of lead paddle 2600. In some embodiments, fluid can be delivered through lumens 2604 and 2606 and the channels through which anchors 2602 pass.

Figure 28A:
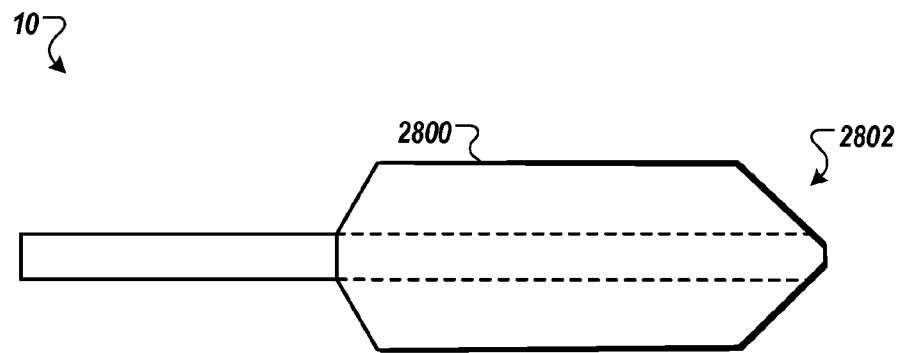
FIGS. 28A-B depict paddle leads used in an electrode system, in accordance with some embodiments.
Figure 28B:
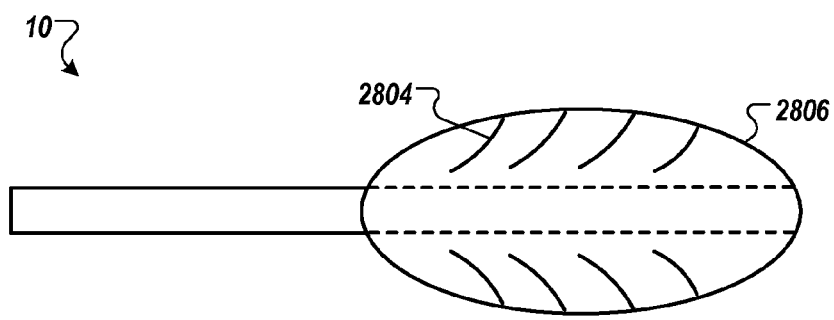

Referring now to FIGS. 28A-B, a lead paddle 2800 can include features to strengthen and/or increase the rigidity of paddle 2800. For example, paddle 2800 can include reinforced distal edges 2802, nitinol ribs 2804, a nitinol frame 2806, and the like.

Referring now to FIGS. 29A-D, an electrode system 10 can include a paddle lead 2900 that can be deployed over a wire 2910. Paddle lead 2900, for example, can be deployed through a flat needle 2920, a round needle 2930, and the like. In some embodiments, paddle lead 2900 is flexible as depicted in FIG. 29D, to fit inside a round needle 2930. Briefly, in use, a needle can be inserted in a patient, and wire 2910 can be advanced into a desired location in the patient. Paddle lead 2900 and a sheath enclosing paddle lead 2900 can be advanced over wire 2910 as described in connection with previous embodiments. The lead can be locked in place, for example, using one of the methods previously described. The sheath and needle can be removed (optionally the wire can be removed), leaving the lead in place. In some embodiments, a shape-memory material, such as nitinol, can be included in the paddle lead 2900, and the lead 2900 can be advanced without the use of a steerable wire.

Figure 30A:
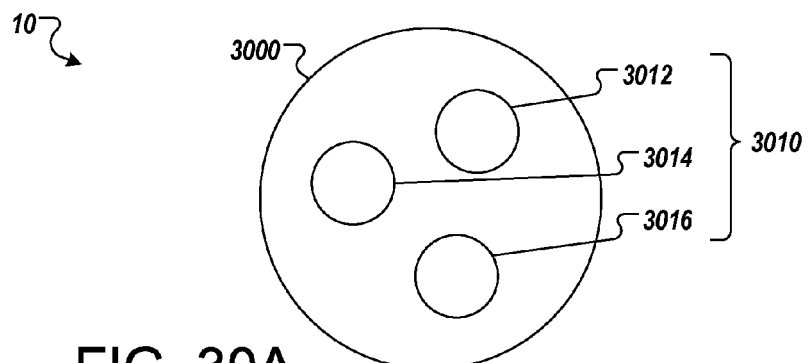
FIG. 30A depicts a multi-lumen lead used in an electrode system, in accordance with some embodiments.

Referring now to FIG. 30A, an electrode system 10 can include a lead 3000 that includes one or more lumens 3010. For example, lead 3000 can include a fluid lumen 3012, a stylet lumen 3014, a wire lumen 3016, and the like. A stylet can be located in the stylet lumen 3014 to add additional stiffness to lead 3000. As described in connection with previous embodiments, a needle can be inserted in a patient, and lead 3000 can be advanced into the distal end of the needle. A wire (e.g., a steerable wire, a nitinol wire, and the like) can be advanced through wire lumen 3016, out the distal end of the wire, and to a desired location in the patient. A stylet can be positioned inside stylet lumen 3014 to add stiffness to lead 3000, and it can be advanced over the wire as described in connection with previous embodiments. The lead can be locked in place, for example, using one of the methods previously described. The needle, stylet, and optionally the wire can be removed, leaving lead 3000 in place.

Figure 31A:
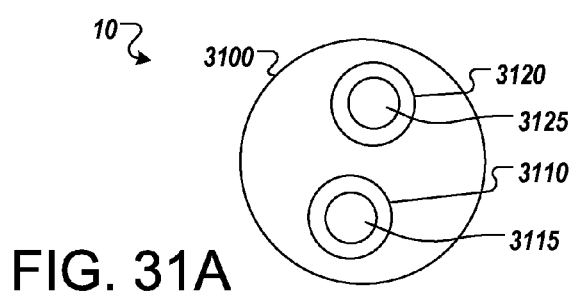
FIGS. 31A-B depict multi-lumen leads, including anchors, used in an electrode system, in accordance with some embodiments.
Figure 31B:
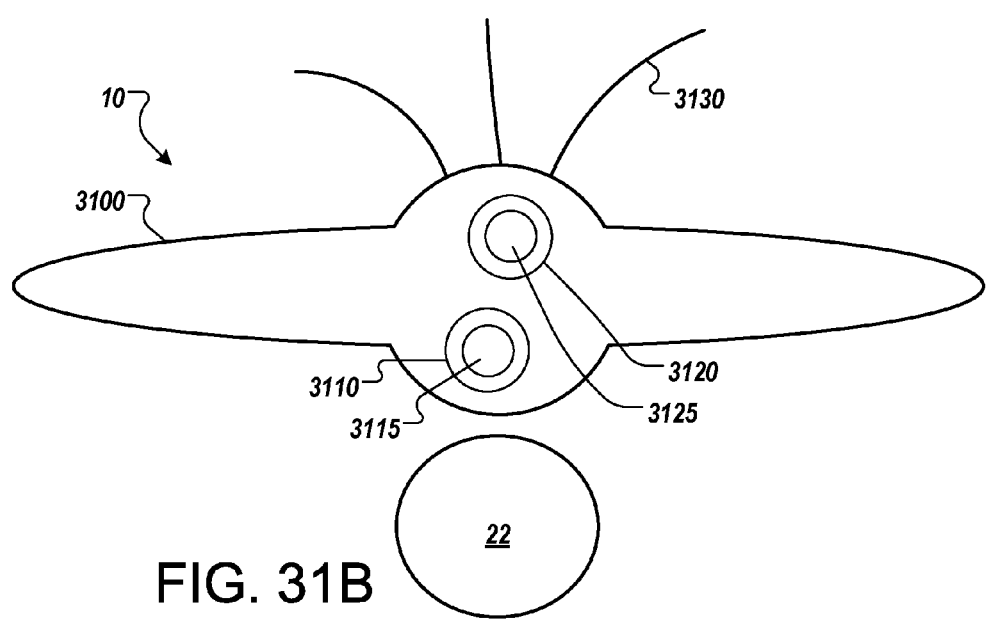

Referring now to FIGS. 31A-B, an electrode system 10 can include a lead 3100 that includes a wire lumen 3110 and an anchor lumen 3120. A wire 3115 can be deployed through wire lumen 3110, and an anchor-deploying device 3125 can be advanced through lumen 3120. Lead 3100 can be positioned above a target tissue (e.g., nerve 22), such that the anchor lumen is opposite nerve 22. When deploying device 3125 is advanced down lumen 3120, anchors 3130 can deploy from lead 3100.

Figure 32A:
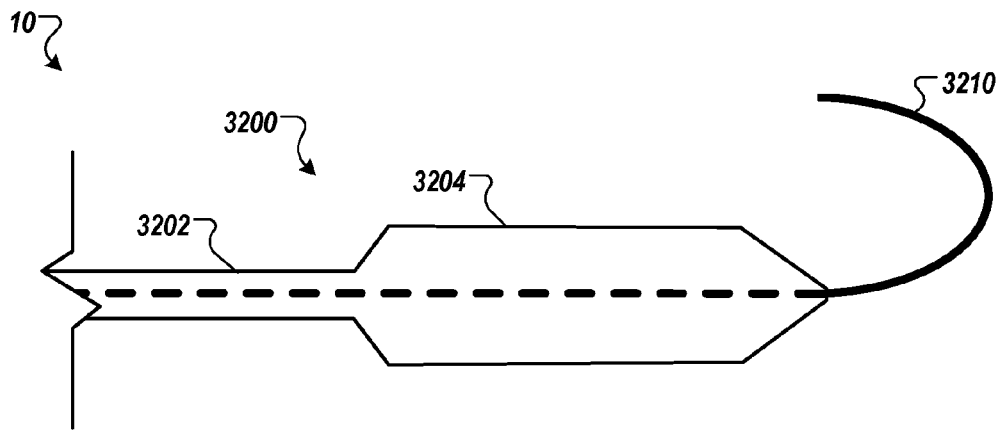
FIGS. 32A-C depict leads used in an electrode system that can be advanced over a wire, in accordance with some embodiments.
Figure 32B:
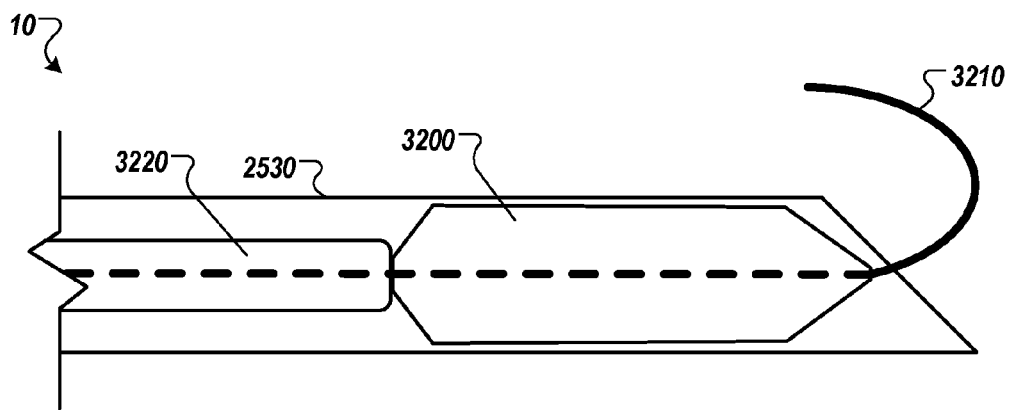
Figure 32C:
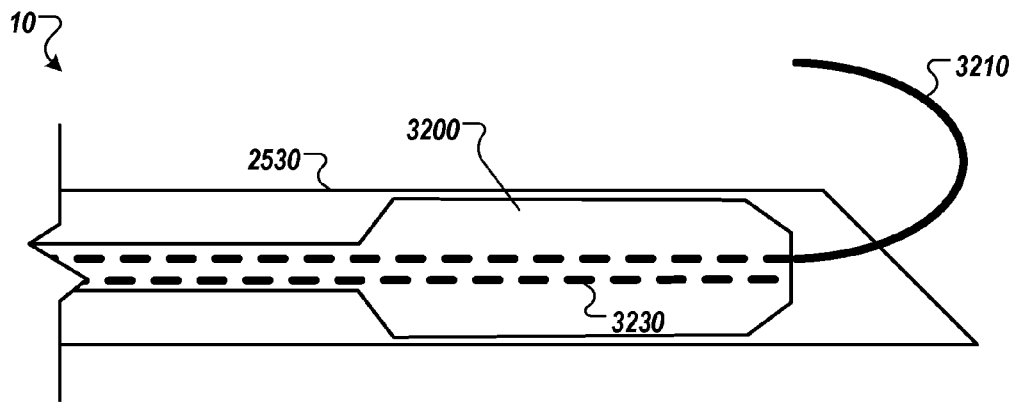

Referring now to FIGS. 32A-C, an electrode system 10 can include features that can assist a lead 3200 in being advanced over a wire 3210. For example, lead 3200 can include a lead shaft 3202 that is thicker or stiffer than a lead head 3204, allowing more force to be applied to lead 3200 when advancing the lead over wire 3210. In some embodiments, a separate pusher 3220 can be used to advance lead 3200 over wire 3200.

In some embodiments, lead 3200 can have multiple lumens such that a first lumen can accept a stylet 3230 to increase the stiffness of lead 3200, while wire 3210 can be passed through a second lumen. In some embodiments, not shown, a stylet with an internal lumen can be inserted into lead 3200, and wire 3210 can be passed through the lumen of the stylet and advance out of the distal end of lead 3200.

In some embodiments, not shown, an electrode system 10 can include a lead with nitinol or nitinol wires integrated with the lead. For example, two nitinol wires can be included on opposing sides of the lead such that the lead and nitinol wires are deployed simultaneously. In some embodiments, nitinol wire included in the lead can allow the lead to be steered without the use of addition wires, and the like.

Referring now to FIG. 33, an electrode system 3300 can include an introducer needle 3310 defining a lumen. Introducer needle 3310 can include a handle region 3315 at a proximal end and a tip 3317 at a distal end. A wire 3320 can be deployed from introducer needle 3310. Upon deployment, wire 3320 can transition into a curved configuration. In some cases, electrode system 3300 can include a shaft 3325. Shaft 3325 can be configured to be attached to lead 3330 and can have a lumen to allow shaft 3325 to track wire 3320. A lead 3330 can be configured to be positioned over wire 3320. As wire 3320 is moved into position relative to target tissue, lead 3330 can also be moved into position. In some cases, lead 3330 can be a narrowing tip structure 3335 at its distal end.

Referring now to FIG. 34, a system provided herein can include an insert device 3400. Insert device 3400 can be configured to be advanced within a lumen of an introducer needle and to hold a wire in proper orientation within the introducer needle. Insert device 3400 can have a shaft portion 3410 and a tip portion 3420. Shaft portion 3410 can be positioned towards a proximal end, and tip portion 3420 can be positioned towards a distal end. The distal end region of insert device 3400 can include an enlarged region 3440. Enlarged region 3440 can be shaped to correspond to the shape of the lumen of an introducer needle. In some cases, enlarged region 3440 can have a groove 3430. Groove 3430 can be configured such that a wire to be deployed can be positioned within groove 3430, thereby holding the wire in a proper orientation while within an introducer needle. As shown in FIG. 35, a system 3500 can include as insert device 3400 positioned within an introducer needle 3310. Insert device 3400 can be used to hold a wire 3320 in a proper configuration while wire 3320 is within introducer needle 3310. Once wire 3320 is deployed from introducer needle 3310, wire 3320 can assume a curved configuration.

Any appropriate type of generator can be used to supply current to the electrodes of a device provided herein. For example, radiofrequency coupled devices or rechargeable/non-rechargeable internal pulse generators can be used to supply current to the electrodes of a device provided herein. In some cases, a lead can be configured to include a microgenerator. For example, a microgenerator can be configured to be part of the same implantable body that contains the electrodes of a device provided herein. Examples of microgenerators that can be used as described herein include, without limitation, those described in U.S. Pat. Nos. 6,061,596, 6,181,965, or Published PCT Application No. WO 97/29802.

The invention will be further described in the following examples, which do not limit the scope of the invention described in the claims.

EXAMPLES

Example 1

Ultrasonic-Guided Percutaneous Placement of Peripheral Nerve Stimulation Electrodes and Anchoring in the Lower Extremity during Simulated Movement Methods Four fresh frozen cadaver lower extremities were thawed for percutaneous electrical lead placement. Using a Toshiba Nemio XG Model SSA-580A ultrasound machine (Toshiba Medical Systems Corp., 1385 Shimoishagami, Otawara-shi, Tochigi-ken, Japan), each cadaver extremity, previously cut off at the midthigh level, was placed in position, and the region of interest scanned with a 14 to 7 MHz linear array transducer. All needles were advanced a few millimeters beyond the visualized nerve, and the leads were placed through the needle until slight tissue resistance was noted, signifying the lead had emerged from the needle tip. The middle of the visualized electrode array was placed near its intersection with the nerve in a perpendicular orientation. The lead was then held in place, as the needle was extracted over the lead. Nerves were scanned in cross section at locations where visualization was satisfactory, then the transducer was gradually moved more proximally or distally. Comparison was made with gross anatomical cross sectional images to define areas where a good acoustical window might exist. The criteria for acceptable placement locations can include: (1) an area that was relatively superficial and where ultrasound guidance and needle placement were possible; (2) the avoidance of vascular structures to the extent possible; (3) minimal traversing of muscular tissue (avoidance of unwanted muscular/motor stimulation effects); (4) the ability to anchor the device in neighboring fascia; and (5) proximal locations for common areas of pathology, such as tarsal tunnel syndrome, common peroneal injury at the fibular head, lateral compartment pain, and distal tibial and peroneal nerve injuries. After several test scans, the following areas were selected: (1) the tibial nerve at a point approximately 8 to 14 cm superior to the medial malleolus, (2) the tibial and peroneal nerves at 2 locations (the popliteal crease, and a point approximately 10 cm superior to the popliteal crease) in the popliteal fossa, and (3) the peroneal nerve at a point 2 to 4 cm inferior to the lateral fibular head.

Once a satisfactory image of the nerve was obtained, a percutaneous 14-gauge epidural needle (Advanced Bionics, Boston Scientific, Valencia, Calif.) was placed under ultrasound guidance, and the 8-contact electrical lead (Advanced Bionics) was advanced through the needle to lie in apposition to the nerve. The needle was directed either immediately superficial to the nerve or deep to the nerve, depending on location, and known anatomical structures. Needles were inserted generally via either an "in plane" technique (needle is placed parallel to the long axis of the transducer) with a short axis/cross sectional view of the nerve, or an "out of plane" technique (needle is placed perpendicular to the long axis of the transducer) in the short axis/cross sectional view. The "in plane" technique allowed direct visualization of the entire shaft of the needle during placement, and was the preferred approach. Electrode visibility during ultrasound scanning was acceptable, often with the ability to identify the individual contacts of the lead. After lead placement, a small incision was made around the electrode and superficial anchoring to nearby fascia was performed. Each lead was dissected to the area of interest to: (1) verify close proximity (within 2 mm) of the lead to the target nerve; and (2) verify no transection or grossly visible injury to the nerve. Two mm was arbitrarily chosen as a reasonable distance based on experience with nonimage-guided percutaneous placement of occipital, supraorbital, and field stimulation trial electrodes. In all cases, the location of scanning was chosen to be proximal to known sites of nerve entrapment or injury.

Results

Tibial Nerve

Figure 16:
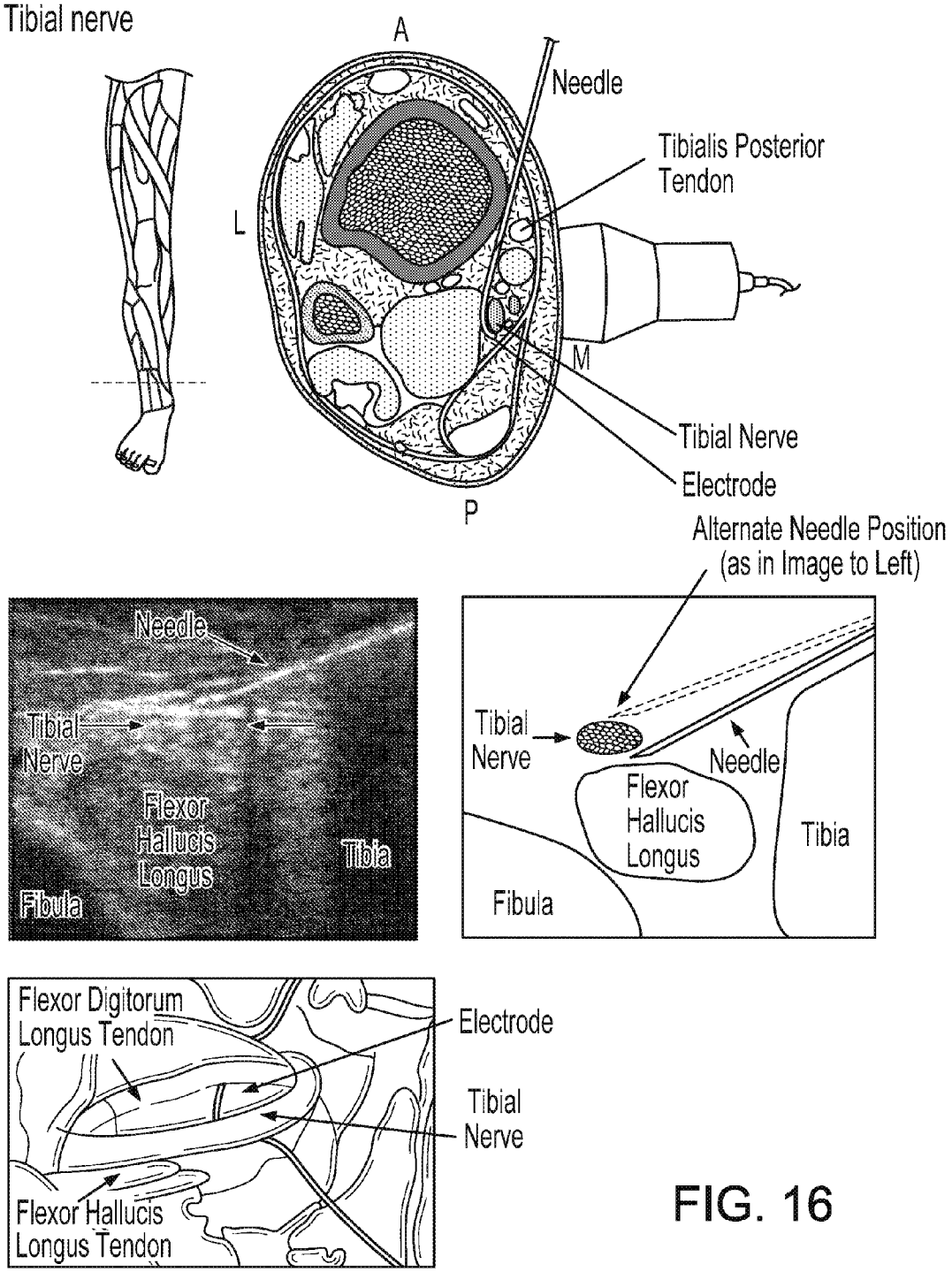
FIG. 16. Upper panel: Illustration of the area approximately 10 cm superior to the medial malleolus in cross section, showing the ultrasound approach utilized to place a peripheral nerve stimulation lead to target the tibial nerve. Note the minimal surrounding musculature. Middle panel: Ultrasound and line drawing showing the needle approaching superficial to the nerve in cross section. Also note the potential for alternate placement either superficial or inferior to the nerve (dotted line). Lower panel: Gross anatomical dissection. One lead contact is seen as the tissue and is slightly retracted after ultrasound-guided placement. The electrode is surrounded by muscle/tendinous structures including the tibialis posterior. Also pictured are the flexor digitorum longus and flexor hallucis longus. In this cadaver, the lead was placed inferior to the overlying nerve. A, anterior; L, lateral; M, medial; P, posterior.

All needle/electrode placements were technically satisfactory (within 2 mm from the nerve). Perpendicular placements of the electrode array, such that electrical contacts 3 and 4 were closest to the nerve, were primarily utilized to allow for possible lead migration. An initial placement was done in the tarsal tunnel on the first cadaver extremity. The tibial nerve was easily visualized with ultrasound using a near field cross axis view proximal to the medial malleolus at this site. Subsequent placements were performed more proximally on the leg. The second needle/electrode was placed also on cadaver 1 using a slightly rotated (approximately 45" in plane with the transducer) approach aiming from posterior to anterior with the needle placed superior to the tibial nerve. Subsequently, the approach depicted (FIG. 16, upper panel) was performed, and utilized on the remaining study specimens. Using an axial cross-sectional view of the nerve approximately 8 to 14 cm above the medial malleolus was considered an appropriate match of the criteria. In this location, the tibial nerve was in close proximity to the posterior tibia at the medial posterior edge. The ultrasound transducer was positioned to visualize the nerve and muscles in cross section, and the needle was passed in line with the transducer from an anterior to posterior direction. Imaging allowed for the demonstration of the hypoechoic tibia, but also the tendons and/or muscular tissue of the tibialis posterior, flexor digitorum longus, and flexor hallucis longus (FIG. 16, upper and middle panels). Both a needle/electrode approach superficial to the tibial nerve (depicted in the ultrasound image, see dotted line, FIG. 16, middle panel, line drawing), and the approach deep to the nerve as seen in the gross anatomical image (FIG. 16, lower panel) seemed reasonable.

Another approach to the tibial nerve was the lower popliteal fossa at the popliteal crease. A lateral to medial approach needle and electrode placement using a short axis view of the nerve and in plane needle placement technique at the popliteal fossa was deemed acceptable. During this initial trial on cadaver 1, the electrode was placed inferior to both the lateral sural and tibial nerves. Later placements were more proximal (high popliteal) as described below.

Sciatic Nerve and Division

Figure 17:
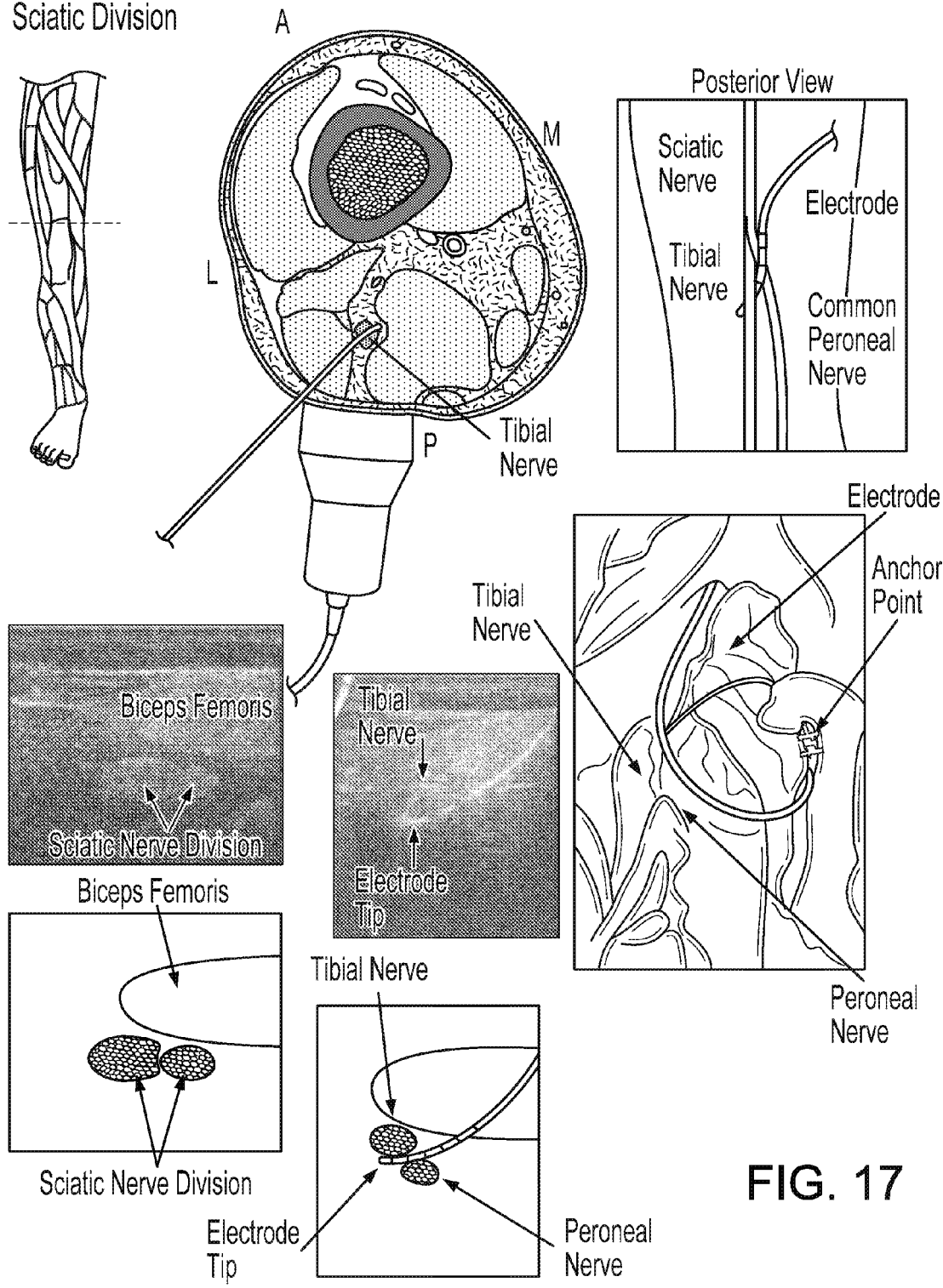
FIG. 17. Upper panel: A cross section illustration through the superior aspect of the popliteal fossa, at the level of the sciatic bifurcation. Note the electrode is depicted as below in the ultrasound image. Alternatives to placement here would allow stimulation of either branches, or the sciatic trunk (above the bifurcation point) at a slightly higher level. Middle panel: Ultrasound image with the sciatic bifurcation noted. The electrode is seen curling under the tibial branch. The peroneal branch is not seen because of the acoustics of the electrode. Note that individual contacts on the lead can be seen. Lower panel: Gross anatomical view. As seen in the other panels, the electrode is seen entering the bifurcation point between the tibial and common peroneal branches. The anchor is noted lateral to muscle fascia. A, anterior; L, lateral; M, medial; P, posterior.

In two cadavers, the tibial nerve was scanned from the popliteal fossa to a point approximately 8 to 12 cm above the popliteal crease where the sciatic nerve initially divides into the tibial and common peroneal nerves (FIG. 17, middle and lower panels). The needle/electrode was passed between the takeoff of both the tibial and common peroneal nerves. Either the sciatic nerve itself, or any of its divisions could be approached at this location. Placement of the lead was performed in one cadaver via an "in plane" needle pass at the bifurcation point (FIG. 17, middle panels). The lead could be seen on gross anatomical section between the two branches of the sciatic nerve (FIG. 17, lower panel).

Peroneal Nerve

The peroneal nerve divides into a superficial and deep branch below the fibular head, and two approaches were considered. In the popliteal approaches described above, the peroneal nerve can be targeted immediately after the sciatic bifurcation approximately 10 cm (variable) above the popliteal crease (FIG. 17, middle panels). The lower popliteal fossa approach to the common peroneal nerve near the popliteal crease was somewhat more significantly hampered by the necessity to advance the needle through the edge of the biceps femoris muscle. This could be overcome by slightly turning the longitudinal axis of the transducer approximately 30 degrees more sagittally, from an inferior to superior needle orientation, adjusting the needle entry point to just medial to the muscle.

The nerve was also approached at a point approximately 2 to 4 cm inferior to the fibular head in cadaver 1 and 2. A short axis, "in plane" technique with the needle entering transversely was acceptable, as the fibula easily could be seen in close proximity to the nerve. This approach to the peroneal nerve inferior to the fibular head made the 8-contact lead length seem less than optimal, as the more proximal 3 to 4 contacts were quite superficial.

Example 2

Ultrasonic-Guided Percutaneous Placement of Peripheral Nerve Stimulation Electrodes and Anchoring in the Upper Extremity During Simulated Movement Methods Three fresh frozen cadaver upper extremities were thawed for percutaneous electrical lead placement. Using a Toshiba Nemio XG Model SSA-580A ultrasound machine (Toshiba Medical Systems Corp., 1385 Shimoishagami, Otawara-shi, Tochigi-ken, Japan), each cadaver extremity, previously cut off at the mid- to upper-humeral level, was examined with a 14 to 7 MHz linear array transducer. Sites chosen for study after anatomical study and ultrasound (US) scanning were: (1) The radial nerve at a point 10 to 14 cm superior to the lateral epicondyle; (2) The median nerve at a point 6 cm distal to the midantecubital fossa; and (3) The ulnar nerve at a point 9 to 13 cm superior to the medial epicondyle. Each nerve was identified using a short axis, cross sectional US view. Sites were chosen to allow proximal placement of electrodes to treat common clinical syndromes, such as ulnar nerve entrapment syndromes, carpal tunnel syndrome, and distal radial nerve injuries. Also considered were: nerve location superficial enough to be easily scanned; the entry locations with respect to ability to anchor the device, and the potential for traversing vascular structures and muscular tissue that might cause unwanted motor stimulation. In each case, the involved target nerve was initially scanned in the short axis view, and the needle was passed in plane longitudinally to the transducer, such that the entire needle shaft could be visualized at all times. More superficial and easily visible locations were chosen, and then scanned more proximally or distally, to find acceptable entry points for needle and electrode. For example, the ulnar nerve was scanned in the ulnar groove, posterior to the medial epicondyle, and then scanning was gradually moved more proximally. The radial nerve was visualized inferior to the spiral groove as it wrapped around the humerus laterally. The median nerve was visualized in the antecubital fossa, and then scanned following the nerve both proximally in the medial arm near the distal humerus, and more distally in the anterior medial forearm. Anatomical cross sectional images were also viewed to consider areas where minimal muscular and tissue barriers might exist.

Once a satisfactory short axis cross section image of the nerve was obtained, a percutaneous 14-gauge epidural needle (Advanced Bionics, Valencia, Calif.) was placed using US guidance, usually going a few millimeters past the nerve. The 8-contact electrical lead (Advanced Bionics) was advanced through the needle until slight tissue resistance was encountered to lie in apposition to the nerve. This placed the electrode array perpendicular to the crossing nerve, with the electrode contacts within approximately 2 mm of the nerve or less, often directly contacting it. Needles were retracted over the leads once the lead had been placed. The needle was directed either immediate, superficial, or deep to the nerve depending on location and known anatomical structures. Needles were advanced in plane with the long axis of the transducer to allow for continuous visualization. After lead placement and superficial anchoring, each lead was dissected to the area of interest to verify: (1) close proximity (within 2 mm) of the lead to the target nerve; and (2) no transection or grossly visible injury to the nerve. In order to simulate upper extremity movement, two of the cadaver extremities were placed in a continuous passive motion (CPM) machine. The extremities then underwent passive motion to 90 degree sat the elbow.

Results

Radial Nerve

Figure 18:
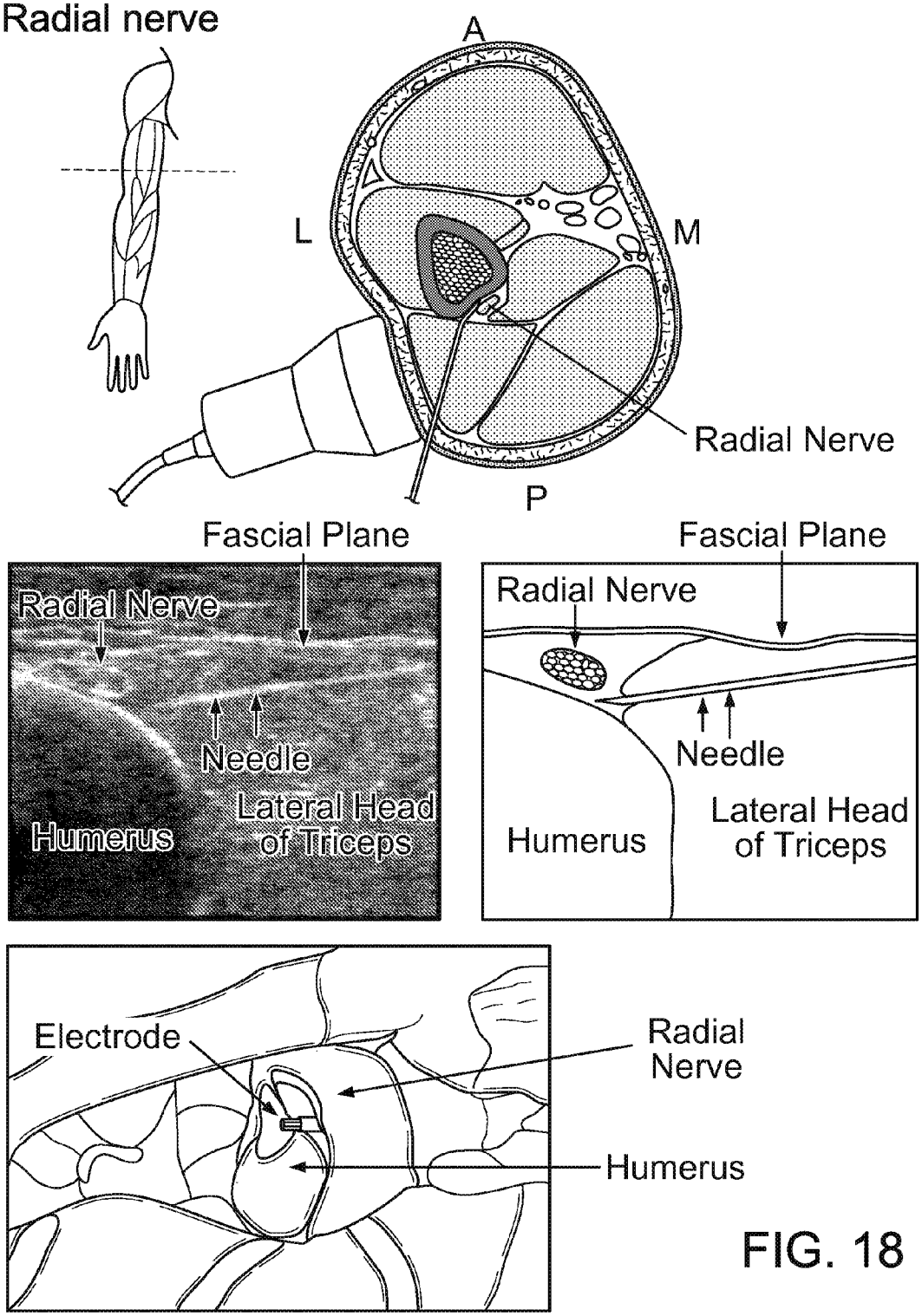
FIG. 18. Upper panel: a cross section through the arm superior to the elbow shows the needle and electrode entry site and technique of placement. Middle panel: the radial nerve is seen as a flattened ovoid structure superior to the humerus approximately 13 cm superior to the lateral epicondyle. An epidural 14-gauge needle designed for spinal stimulation applications is advanced toward the interface of the humerus and radial nerve. To the right of the ultrasound image, a line drawing of the ultrasound view is seen. Lower panel: gross anatomical dissection of the lead shown in the above figures, with the lead contacts clearly seen between the humerus and radial nerve. A, anterior; L, lateral; M, medial; P, posterior.

All three placements were technically satisfactory within 2 mm from the nerve, and perpendicular placements were used to allow for possible lead migration and optimized electrical contact. The location approximately 10 to 14 cm above the lateral epicondyle allowed easy visualization. A short axis view of the nerve was easy to visualize. In this location, the slightly ovoid and flattened radial nerve is in close proximity to the humerus (FIG. 18, upper panel). The bone/nerve interface allowed the needle to be placed immediately deep to the nerve until the humerus was gently contacted. The needle shaft then was used to gently "lift" the nerve to slide the needle between the humerus the nerve (FIG. 18, middle panels). Once the needle had passed between the humerus and the nerve, the electrode was passed through the needle until tissue resistance was encountered. Minimal muscular tissue exists at this tissue plane. Anatomical dissection after placement demonstrated no apparent neural injury or intraneural placement (FIG. 18, lower panel). After 21 hours of CPM, the radial nerve electrodes were re-examined and found to be in a stable position (no migration).

Ulnar Nerve

The approach to the ulnar nerve was hamperedby the necessity to advance the needle through neighboring medial triceps muscular tissue planes; however, this also allowed for a tissue buffer between the lead and the nerve (FIG. 19, upper and middle panels). The ulnar nerve at a point 9 to 13 cm superior to the medial epicondyle is easily visualized, and can be traced with US, cephalad from the ulnar condylar groove as it lies close to the humerus.

In one case, the needle (and electrode) was placed superficial to the nerve, and in two cases the needle was placed deep to the nerve from lateral to medial (FIG. 19, middle and lower panels). Placements deep to the nerve, from anterior to posterior (resulting in a perpendicular orientation to the nerve), allowed a small tissue buffer between the nerve and the electrode. After CPM, the electrodes in two of the extremities were inspected. In one extremity, the electrode showed no migration (contacts 3 and 4 were in close proximity to the ulnar nerve pre- and post-CPM). In the second extremity the electrode showed slight migration (contacts 2 and 3 were in close proximity to the ulnar nerve pre-CPM, and contacts 1 and 2 were in close proximity to the ulnar nerve post-CPM).

Median Nerve

The median nerve was identified in the antecubital fossa where it could easily be visualized medial to the brachial artery. The nerve was then traced approximately 6 to 8 cm cephalad. The nerve was also easily visualized at a point approximately 6 cm distal to the antecubital fossa. Either position seemed to be a reasonable approach, given the superficial location, and background anatomical structures. The potential for migration for the more inferior placement seemed less likely during elbow flexion, compared with an approach at the midantecubital fossa as well. The location inferior to the antecubital fossa afforded minimal muscle tissue between the target nerve and skin surface. The median nerve in the upper third of the forearm is inferior to the pronator teres muscle and fascia medial to the interosseus artery. All three electrode placements, using the location approximately 6 cm inferior to a line drawn between the humeral epicondyles, were found on dissection to be within 2 mm of the nerve without detectable neural injury. Some muscular tissue (pronator teres and flexor group) was split by the needle and electrode. A slightly tangential approach in plane with the US probe turned, such that the lateral edge was more inferior, aiming from medial to lateral, was favored. An out of plane approach may have more easily missed muscular tissue, but the needle shaft would have been out of plane as well. Two of the cadaver extremities were examined after CPM for 21 hours. In the first cadaver, the electrode migrated resulting in the median nerve overlying the first contact only (prior to CPM the second and third contacts were in close proximity to the median nerve). In a clinical scenario, this would have likely resulted in a loss of paresthesia coverage. The second cadaver also showed migration but to a lesser extent. In this cadaver, the median nerve was overlying the second and third contacts, and after CPM was overlying the first and second contacts.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing peripheral nerve stimulation, wherein said method comprises:
    (a) percutaneously advancing a tubular member defining a lumen to a peripheral nerve within a mammal,
    (b) advancing a wire through said lumen of said tubular member and at least 180 degrees around said peripheral nerve,
    (c) advancing a lead comprising an electrode over said wire to position said lead at least 180 degrees around said peripheral nerve, and
    (d) applying electrical stimulation to said peripheral nerve via said electrode.

2. The method of claim 1, wherein said lead is not in contact with said peripheral nerve when positioned at least 180 degrees around said peripheral nerve within said mammal.

3. The method of claim 1, wherein said method comprises advancing said lead over said wire to position said lead at least 270 degrees around said peripheral nerve within said mammal.

4. The method of claim 1, wherein said lead comprises an echogenic material or an echogenic marking.

5. The method of claim 4, wherein said lead is implanted into position within said mammal using ultrasound-guided placement.

6. The method of claim 1, wherein said lead comprises a shape-memory material.

7. The method of claim 6, wherein said shape-memory material is nitinol.

8. The method of claim 1, wherein no more than one skin port is used to percutaneously advance said tubular member to said peripheral nerve and to advance said wire at least 180 degrees around said peripheral nerve.

9. The method of claim 1, wherein two skin ports are used to percutaneously advance said tubular member to said peripheral nerve and to advance said wire at least 180 degrees around said peripheral nerve.

10. The method of claim 1, wherein said lead defines a lumen.

11. The method of claim 10, wherein said method comprises withdrawing said wire from said mammal after said lead is advanced over said wire.

12. A method for providing electrical stimulation or an agent to tissue, wherein said method comprises:

(a) percutaneously advancing a tubular member defining a lumen to a peripheral nerve within a mammal, (b) advancing a wire through said lumen of said tubular member and at least 180 degrees around said peripheral nerve, (c) advancing a lead comprising an electrode or the ability to release an agent over said wire to position said lead at least 180 degrees around said peripheral nerve, and (d) applying electrical stimulation to said target tissue via said electrode or applying said agent to said target tissue.

13. The method of claim 12, wherein said target tissue is a peripheral nerve.

14. The method of claim 12, wherein said method comprises percutaneously wrapping said lead at least 270 degrees around said target tissue within said mammal.

15. The method of claim 12, wherein said lead comprises an echogenic material or an echogenic marking 16. The method of claim 15, wherein said lead is implanted into position within said mammal using ultrasound-guided placement.

17. The method of claim 12, wherein said lead defines a lumen.

18. The method of claim 17, wherein said method comprises withdrawing said wire from said mammal after said lead is advanced over said wire.

* * * * *

UNITED STATES PATENT AND TRADEMARK OFFICE
CERTIFICATE OF CORRECTION

| | | |
|---|---|---|
| PATENT NO. | : 8,929,998 B2 | Page 1 of 1 |
| APPLICATION NO. | : 13/498873 | |
| DATED | : January 6, 2015 | |
| INVENTOR(S) | : Abram H. Burgher and Marc A. Huntoon | |

It is certified that error appears in the above-identified patent and that said Letters Patent is hereby corrected as shown below:

In the Specification,

Column 1, line 8, please delete "371" and insert -- §371 --, therefor;

Column 1, line 8, please delete "119(a)" and insert -- §119(a) --, therefor;

In the Claims,

Column 18, line 18 (Claim 15), please delete "marking" and insert -- marking. --, therefor.

Signed and Sealed this
Sixteenth Day of June, 2015

Michelle K. Lee
*Director of the United States Patent and Trademark Office*